(12) United States Patent
Pataki et al.

(10) Patent No.: US 11,927,507 B2
(45) Date of Patent: Mar. 12, 2024

(54) SAMPLING DEVICE

(71) Applicant: Pharma and Nutraceutical PD Pty Ltd, Collaroy (AU)

(72) Inventors: Attila Pataki, Collaroy (AU); Sean Kim Pataki, Collaroy (AU)

(73) Assignee: PHARMA AND NUTRACEUTICAL PD PTY LTD, South Wales (AU)

( * ) Notice: Subject to any disclaimer, the term of this patent is extended or adjusted under 35 U.S.C. 154(b) by 606 days.

(21) Appl. No.: 17/046,919

(22) PCT Filed: Apr. 12, 2019

(86) PCT No.: PCT/AU2019/050332
§ 371 (c)(1),
(2) Date: Oct. 12, 2020

(87) PCT Pub. No.: WO2019/195895
PCT Pub. Date: Oct. 17, 2019

(65) Prior Publication Data
US 2021/0190644 A1 Jun. 24, 2021

(30) Foreign Application Priority Data
Apr. 12, 2018 (AU) .................... 2018901227

(51) Int. Cl.
*G01N 1/16* (2006.01)
*B01L 3/18* (2006.01)
(Continued)

(52) U.S. Cl.
CPC .................. *G01N 1/16* (2013.01); *B01L 3/18* (2013.01); *G01F 11/24* (2013.01); *G01N 33/00* (2013.01); *G01N 2033/0091* (2013.01)

(58) Field of Classification Search
CPC .. G01N 1/16; G01N 33/00; G01N 2033/0091; G01N 2001/1006; G01N 1/08; G01N 1/02; B01L 3/18; B01L 3/502715; B01L 3/502761; G01F 11/24
See application file for complete search history.

(56) References Cited

U.S. PATENT DOCUMENTS

| 176,038 A | 4/1876 | Nelson |
| 455,733 A | 7/1891 | Bell |
| (Continued) |

FOREIGN PATENT DOCUMENTS

| CA | 2101390 | 1/1995 |
| CA | 2124099 | 9/1995 |
| (Continued) |

OTHER PUBLICATIONS

Australian International-type search for provisional patent application dated May 24, 2018, 13 pages.
(Continued)

*Primary Examiner* — Jennifer Wecker
*Assistant Examiner* — Jonathan Bortoli
(74) *Attorney, Agent, or Firm* — Morgan, Lewis & Bockius LLP

(57) ABSTRACT

This invention relates to a sampling device. The device includes an elongate separating member having a sampling side and a non-sampling side. One or more through openings extend from the sampling side to the non-sampling side of the elongate member. The separating member is adapted for insertion into a reservoir of particulate material so as to define a sampling zone and a non-sampling zone within the reservoir. A shaft is positioned away from the sampling side and operably associated with the separating member, wherein the shaft is selectively rotatable about its longitudinal axis. One or more sample capturing scoops are attached to the shaft so as to be aligned with a respective opening. The or each scoop has a leading edge, a trailing
(Continued)

edge and a cavity for receiving a sample of particulate material. The device is configured such that rotation of the shaft about its longitudinal axis causes a corresponding rotation of the or each scoop between a first position and a second position. In the first position, the leading edge of the associated scoop is located within the respective opening such that the opening is effectively closed and the remainder of the scoop projects away from the sampling side such that the sampling side of the separating member is free of protuberances during insertion into the reservoir. In the second position, the scoop is positioned on the sampling side and the leading edge of the associated scoop bears against the sampling side of the elongate member, thereby to enclose the sample of particulate material by the rotation of the scoop towards the second position.

20 Claims, 12 Drawing Sheets

(51) Int. Cl.
*G01F 11/24* (2006.01)
*G01N 33/00* (2006.01)

(56) References Cited

U.S. PATENT DOCUMENTS

| | | |
|---|---|---|
| 1,078,847 A | 11/1913 | Grauenfels |
| 1,109,446 A | 9/1914 | Melberg |
| 2,185,386 A | 1/1940 | Valentine |
| 2,185,651 A | 1/1940 | Sollie |
| 2,283,650 A | 5/1942 | Sanborn |
| 2,844,036 A | 7/1958 | Wright |
| 2,875,615 A | 3/1959 | Ulvin |
| 3,080,760 A | 3/1963 | Piersma |
| 3,091,969 A | 6/1963 | Romanchuk et al. |
| 3,158,109 A | 11/1964 | Stott |
| 3,218,869 A | 11/1965 | Fields et al. |
| 3,326,049 A | 6/1967 | Eley |
| 3,528,294 A | 9/1970 | Manevy |
| 3,575,055 A | 4/1971 | Thornton, Jr. |
| 3,595,088 A | 7/1971 | Meunier |
| 3,667,512 A | 6/1972 | Jackson |
| 3,802,270 A | 4/1974 | Daniels et al. |
| 3,875,803 A | 4/1975 | Clewlow |
| 3,943,771 A | 3/1976 | Handa et al. |
| 4,022,065 A | 5/1977 | Ramin et al. |
| 4,023,716 A | 5/1977 | Shapiro |
| 4,055,088 A | 10/1977 | Diss |
| 4,056,360 A | 11/1977 | Risch |
| 4,062,386 A | 12/1977 | Zanasi |
| 4,072,059 A | 2/1978 | Hamilton |
| 4,082,003 A | 4/1978 | Hentschell, Jr. et al. |
| 4,116,247 A | 9/1978 | Zanasi |
| 4,141,251 A | 2/1979 | Oshikubo |
| 4,148,315 A | 4/1979 | Berezkin et al. |
| 4,172,385 A | 10/1979 | Cristensen |
| 4,283,946 A | 8/1981 | Bowser et al. |
| 4,361,052 A | 11/1982 | Nicol et al. |
| 4,442,721 A | 4/1984 | Singer |
| 4,518,076 A | 5/1985 | Feisel et al. |
| 4,528,161 A | 7/1985 | Eckert |
| 4,549,612 A | 10/1985 | Cushing |
| 4,580,577 A | 4/1986 | O'Brien et al. |
| 4,632,411 A * | 12/1986 | Badger ............. B62B 3/14 |
| | | 280/33.991 |
| 4,640,614 A | 2/1987 | Roberts et al. |
| 4,660,423 A | 4/1987 | Armstrong et al. |
| 4,685,339 A | 8/1987 | Philipenko |
| 4,744,256 A | 5/1988 | Niskin |
| 4,750,373 A | 6/1988 | Shapiro |
| 4,790,198 A | 12/1988 | Awtry et al. |
| 4,800,765 A | 1/1989 | Nelson |
| 4,840,517 A | 6/1989 | Bullivant |
| 4,951,511 A | 8/1990 | Perron et al. |
| 4,989,678 A | 2/1991 | Thompson |
| 5,045,286 A | 9/1991 | Kitajima et al. |
| 5,063,025 A | 11/1991 | Ito |
| 5,272,926 A | 12/1993 | Wilkins |
| 5,289,727 A | 3/1994 | Earle et al. |
| 5,337,620 A | 8/1994 | Kalidini |
| 5,343,771 A | 9/1994 | Turriff et al. |
| 5,377,551 A | 1/1995 | Vacquer |
| 5,398,557 A | 3/1995 | Shimizu et al. |
| 5,440,941 A | 8/1995 | Kalidindi |
| 5,470,535 A | 11/1995 | Ray et al. |
| 5,474,140 A | 12/1995 | Stevens |
| 5,476,017 A | 12/1995 | Pinto et al. |
| 5,478,526 A | 12/1995 | Sakai et al. |
| 5,492,021 A | 2/1996 | Bourgeois et al. |
| 5,512,248 A | 4/1996 | Van |
| 5,703,301 A | 12/1997 | Pinto et al. |
| 5,996,426 A | 12/1999 | Robinson et al. |
| 6,054,099 A | 4/2000 | Levy |
| 6,094,999 A | 8/2000 | DuBois |
| 6,171,280 B1 | 1/2001 | Imazu et al. |
| 6,339,966 B1 | 1/2002 | Kalidindi |
| 6,393,926 B1 | 5/2002 | Bowersox, Jr. et al. |
| 6,631,650 B1 | 10/2003 | Espinosa |
| 6,644,137 B1 | 11/2003 | Bellamy et al. |
| 6,910,393 B2 | 6/2005 | Muzzio et al. |
| 6,991,714 B1 * | 1/2006 | Gauss ............. B26F 1/04 |
| | | 422/69 |
| 7,168,332 B2 | 1/2007 | Orange et al. |
| 8,650,974 B2 | 2/2014 | Pritzke |
| 9,702,815 B2 | 7/2017 | Dalal et al. |
| 2003/0221495 A1 | 12/2003 | Muzzio et al. |
| 2006/0048587 A1 | 3/2006 | Orange et al. |
| 2006/0175089 A1 * | 8/2006 | Nance ............. G01N 1/08 |
| | | 175/246 |
| 2008/0182340 A1 | 7/2008 | Lemmo |
| 2010/0011889 A1 | 1/2010 | Lemmo |
| 2011/0000322 A1 | 1/2011 | Chen et al. |
| 2011/0049198 A1 | 3/2011 | Muth |
| 2015/0129764 A1 | 5/2015 | Dalal et al. |
| 2016/0363512 A1 | 12/2016 | Fenner et al. |

FOREIGN PATENT DOCUMENTS

| | | |
|---|---|---|
| CN | 2709976 Y | 7/2005 |
| CN | 101169353 | 4/2008 |
| CN | 101231219 A | 7/2008 |
| CN | 203337414 U | 12/2013 |
| CN | 103543035 B | 1/2014 |
| CN | 103837377 A | 6/2014 |
| CN | 203705183 U | 7/2014 |
| CN | 204027866 U | 12/2014 |
| CN | 204085923 U | 1/2015 |
| CN | 104359703 A | 2/2015 |
| CN | 104807672 A | 7/2015 |
| CN | 204536056 U | 8/2015 |
| CN | 204964243 U | 1/2016 |
| CN | 205067151 U | 3/2016 |
| CN | 205157224 U | 4/2016 |
| CN | 105588735 A | 5/2016 |
| CN | 105606406 A | 5/2016 |
| CN | 205506453 U | 8/2016 |
| CN | 205861386 U | 1/2017 |
| CN | 205941062 U | 2/2017 |
| CN | 206095706 U | 4/2017 |
| JP | 2004309253 | 11/2004 |
| WO | 1998018558 A1 | 5/1998 |

OTHER PUBLICATIONS

Muzzio et al. "Sampling practices in powder blending", International Journal of Pharmaceutics, 1997, pp. 153-178.
Muzzio et al. "Sampling and characterization of pharmaceutical powders and granular blends", International Journal of Pharmaceutics, sciencedirect.com, 2003, 250, pp. 51-64.

(56) References Cited

OTHER PUBLICATIONS

Ebensen et al. "Adequacy and verifiability of pharmaceutical mixtures and dose units by variographic analysis (Theory of Sampling)—a call for a regulatory paradigm shift", International Journal of Pharmaceutics, www.elsevier.com/locate/ijpharm, 2016, 499, pp. 156-174.
Burkle, Catalog—Pumps | Sampling | Plastic Labware for Laboratory, Industry, Science, 2018, 23 pages.
Sampling Systems, Catalog—World Class Equipment worldwide, Edition K, www.sampling.com, 2017, 43 pages.
Globe Pharma—Catalog—Powder Samplers, www.globepharma.com, 9 pages.
International Search Report and Written Opinion for International Patent Application No. PCT/AU2019/050332, 11 pages.
Muzzio, et al., "Sampling practices in powder blending," International Journal of Pharmaceutics 155 (1997) 153-178.
Esbensen, et al., "Adequacy and verifiability of pharmaceutical mixtures and dose units by variographic analysis (Theory of Sampling)—A call for a regulatory paradigm shift," International Journal of Pharmaceutics 499 (2016) 156-174.

* cited by examiner

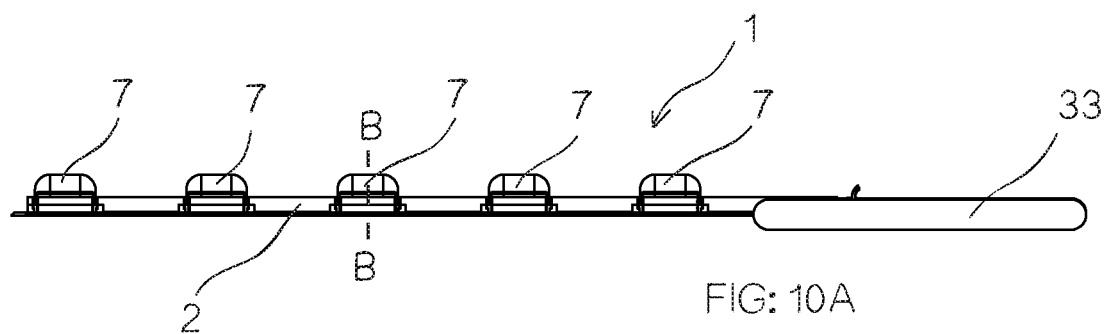
FIG: 10A
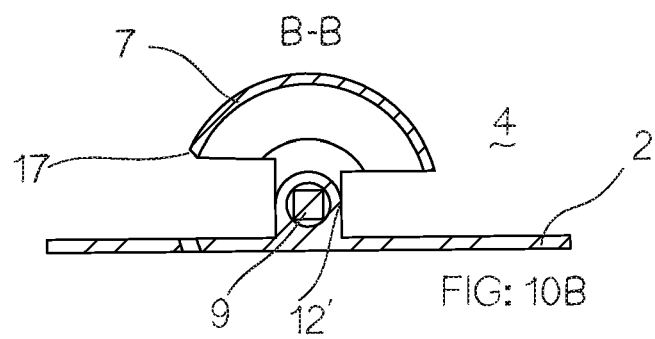
FIG: 10B
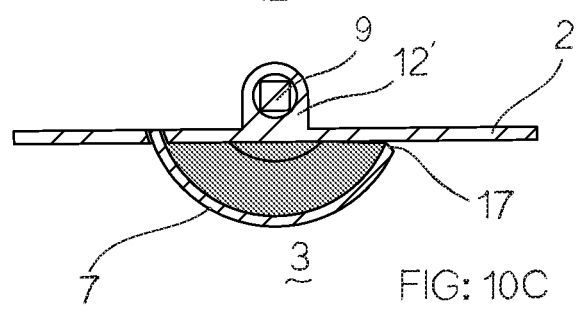
FIG: 10C
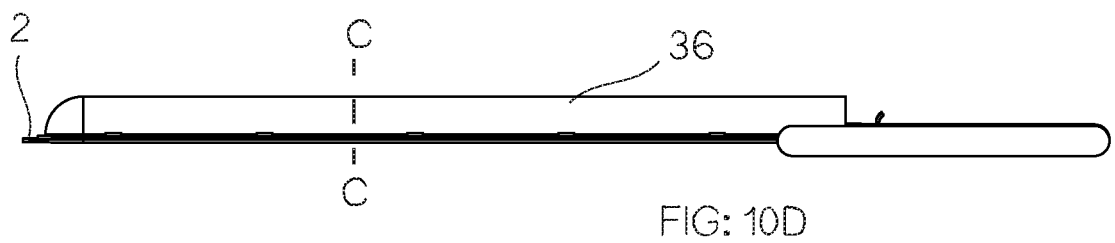
FIG: 10D
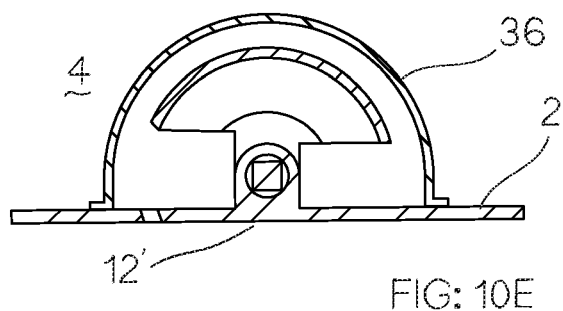
FIG: 10E

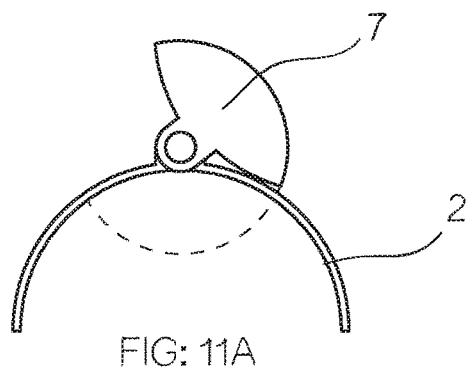
FIG: 11A
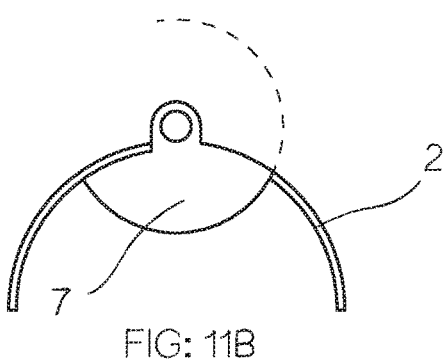
FIG: 11B
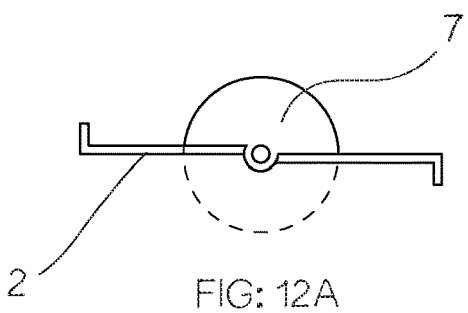
FIG: 12A
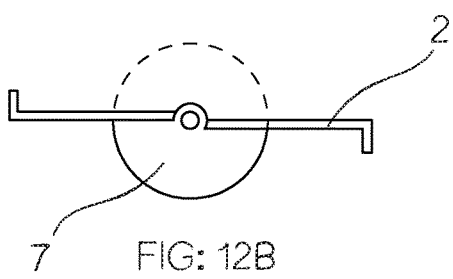
FIG: 12B
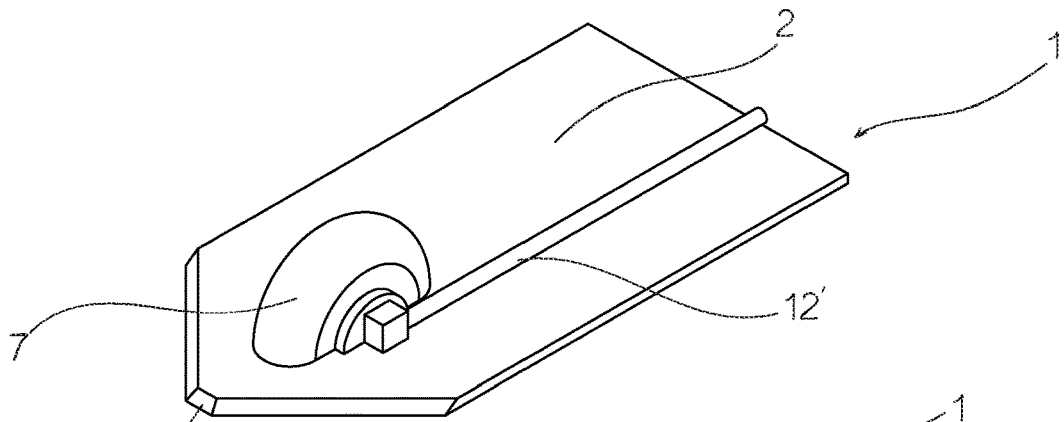
FIG: 13
FIG: 14

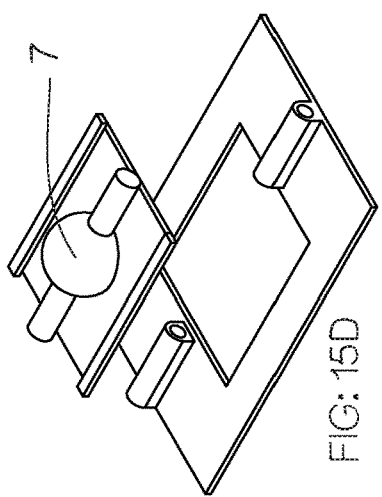
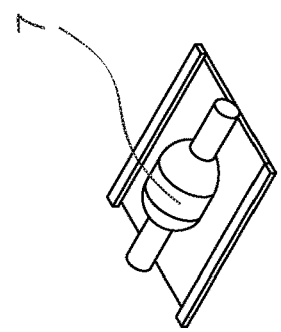
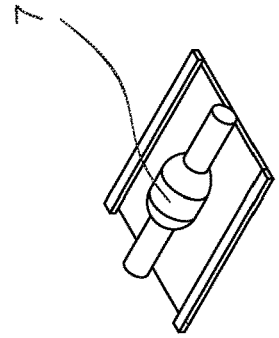
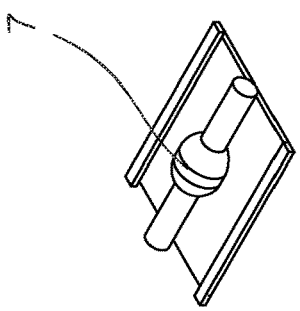
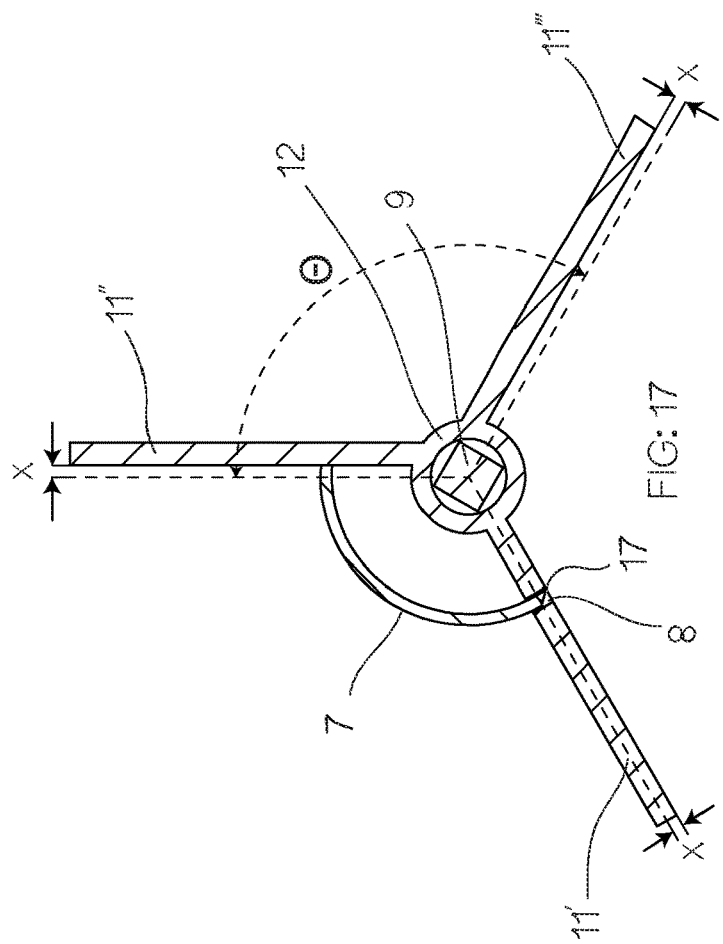
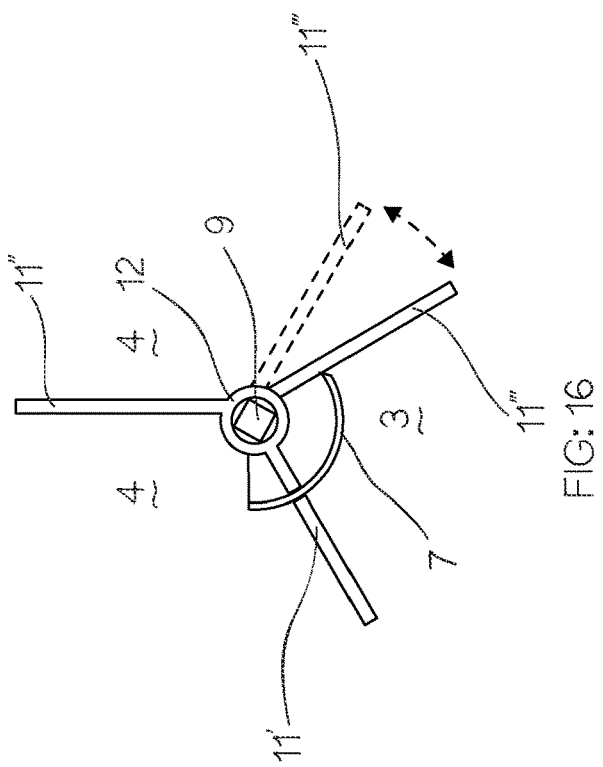

SAMPLING DEVICE

This application is a U.S. National Phase of International Application No. PCT/AU2019/050332 filed on Apr. 12, 2019, which claims the benefit of Australian Patent Application No. 2018901227 filed Apr. 12, 2018, each of which is incorporated by reference herein in its entirety.

FIELD OF THE INVENTION

The present invention relates to sampling devices. More particularly the invention relates to devices for sampling of particulate materials such as powder blends, especially pharmaceutical blends.

The invention has been developed primarily for use as a powder sampling device for conducting unit dose related volume sampling of free-flowing or cohesive pharmaceutical powder or granule mixtures from mixers, blenders or storage containers and will be described predominantly in this context. However, it will be appreciated that the invention is not limited to this particular field of use, being potentially applicable in a wide variety of applications where samples of particulate materials are required.

BACKGROUND OF THE INVENTION

The following discussion of the prior art is intended to facilitate an understanding of the invention and to enable the advantages of it to be more fully understood. It should be appreciated, however, that any reference to prior art throughout the specification should not be construed as an express or implied admission that such prior art is widely known or forms part of common general knowledge in the field.

The manufacturing of solid pharmaceutical dosage forms commonly involves a process of mixing actives and inactive ingredients (excipients). It is essential that the actives and excipients are uniformly distributed within the blend to allow accurate delivery of dosage in the final form, which may be a tablet, capsule, pill, powder or other such delivery means.

Validation of manufacturing processes requires demonstration of adequate control over predetermined characteristics of the process output. Pharmaceutical manufacturers must validate their processes for compliance with various regulatory requirements, for example, Current Good Manufacturing Practice regulations (CGMPs) stipulated by the Federal Food, Drug and Cosmetic Act in the United States.

Validation of pharmaceutical mixing processes requires routine testing of blend uniformity (or homogeneity). However, in spite of the well-recognised importance of evaluation of blend homogeneity, there is no industry-wide consensus on how to conduct such tests and currently available sampling devices cannot collect the desired samples without disturbing the granule bed and thus altering the composition of the collected samples.

Despite these difficulties in satisfactorily delivering content uniformity testing being recognised since the 1993 Barr Judgment (United States v. Barr Labs, Inc. 812 F. Supp 458, D.N.J. 1993), these issues remain a problem today in current sampling practices throughout the pharmaceutical industry.

Presently available sampling devices are often spear shaped, having an elongate rod portion with a pointed end and require particles to flow into cavities within the rod. Such devices are known as "sampling thieves" or "thief probes".

The construction of these thief sampling probes give rise to a number of inherent problems which result in errors and inconsistency when taking samples, including, but not limited to: (i) the diameter of the probe pushes particles during insertion, concentrating fine particles closer to the probe, (ii) the sample entry cavities on the outer sleeve entrap particles (mainly fines) from the above layers and drag them down, thereby contaminating the collected samples, and (iii) problems relating to flow capture such as the need for the particles to flow into the sampling cavities creates further composition alteration as it favours fine particles, incomplete sample cavity filling can arise even when the granules have relatively good flow property particularly deeper down in the granules bed due to pressure. In use, the position and/or orientation of the sampling thief within a reservoir of particulate material can influence the volume of the sample collected and the composition of the sample obtained can be influenced by the skill of the operator. In addition, thief probes are not suitable for use in sampling cohesive powder.

Other types of samplers include tube-shaped "core samplers". While these generally do not require the powder material to flow, they are often limited to collecting one sample only (end samplers). Further, some require an external closing mechanism in free-flowing granules which disturbs the granule bed, thus diminishing the reliability of a second sample from the same area.

Some tube-shaped core-samplers collect a continuous column of sample. However, such samplers may cause vertical mixing of the sample layers due to friction on the inside wall of the tube during collection and also during ejection of the sample. These samplers may also require an external closing mechanism, further disturbing the granules.

Thus, these devices are subject to a number of inherent disadvantages and a solution or alternative is required. It is an object of the present invention to overcome or ameliorate at least one of the disadvantages of the prior art, or to provide a useful alternative.

SUMMARY OF THE INVENTION

In general terms, the underlining design principle of the present invention is to separate any disturbance the insertion of a sampling device or probe causes to a granule bed from the area targeted for sampling (i.e. the sampling zone) and to capture a sample without forcing or otherwise requiring the particles within the sampling zone to move. In broad terms, this is achieved by introducing an elongate separating member (e.g. in the simplest embodiment resembles a large thin spatula or plate) that, when the device is inserted into the granule bed, separates the granule bed into sampling and non-sampling zones. The sampling side of the separating member (i.e. the side facing towards the sampling zone) is advantageously smooth and free of any protrusions during insertion. Prior to and during insertion, all the mechanical elements necessary for sampling are contained in or positioned on the non-sampling side of the separating member (i.e. the side facing towards the non-sampling zone). As described further below, the mechanical elements include a rotational shaft and one or more thin shelled sampling scoops, which are preferably rotationally symmetrical. Preferably, there are tightly fitting thin precision cuts on the separating plate that allow the scoops to be turned to the sampling side upon rotation of the shaft. When that happens, the samples are captured by the scoop without the need for the particles to move. A locking device is preferably provided for releasably locking the position of the shaft so that the captured samples can be safely withdrawn when the sampler is removed from the granule bed and subsequently placed in a horizontal position on an emptying rack, where the samples can be transferred into collection containers.

Accordingly, in one aspect of the invention there is provided a sampling device, including:
- an elongate separating member having a sampling side and a non-sampling side, the elongate member having one or more through openings extending from the sampling side to the non-sampling side, the separating member being adapted for insertion into a reservoir of particulate material, thereby to define a sampling zone and a non-sampling zone within the reservoir;
- a shaft operably associated with the separating member, the shaft being positioned away from the sampling side and selectively rotatable about its longitudinal axis; and
- one or more sample capturing scoops attached to the shaft so as to be aligned with a respective opening, the or each scoop having a leading edge, a trailing edge and a cavity for receiving (or enveloping) a sample of particulate material;
- wherein rotation of the shaft about its longitudinal axis causes a corresponding rotation of the or each scoop between a first position (the non-sampling position) in which the leading edge of the associated scoop is located within the respective opening such that the opening is effectively closed and the remainder of the scoop projects away from the sampling side such that sampling side of the separating member is free of protuberances during insertion into the reservoir, and a second position (the sampling position) in which the scoop is positioned on the sampling side and the leading edge of the associated scoop bears against the sampling side of the elongate member, thereby to enclose the sample of particulate material by the rotation of the scoop towards the second position.

Preferably, the leading edge of the associated scoop is substantially flush with a surface of the sampling side when the scoop is in its first position, thereby to inhibit the ingress of powder into or through the opening.

Preferably, the trailing edge of each scoop bears against a surface of the non-sampling side of the separating member when the scoop is in its first position, thereby to inhibit the ingress of powder into the cavity of the scoop during insertion of the device into a reservoir of particulate material. When the scoop is in its second position, the trailing edge of each scoop is preferably located within the respective opening such that the opening is effectively closed and a predetermined sample volume of the particulate material is encapsulated by the scoop and the respective portion of the sampling side surface of the separating member.

Preferably, each scoop has a top surface, a bottom surface and a side wall extending between the top surface and bottom surface, thereby to define the cavity for receiving or encapsulating the particulate material (i.e. upon rotational movement of the scoop, rather than flow or other movement of the particulate material). Each scoop preferably has an opening to allow passage of the particulate material into the cavity, wherein the opening has a periphery defined by the leading edge, the trailing edge, the front end of the top surface and the front edge of the bottom surface of the associated scoop.

Preferably, each opening in the separating member is configured to ensure substantially size-for-size matching with the profile of the respective scoop, whereby the opening is effectively closed when the leading or trailing edge of the scoop is received within the opening, and to allow passage of the scoop through the opening upon rotation of the shaft.

In some embodiments, each opening is in the form of thin precision cuts on the separating member. In certain embodiments, the openings may be substantially C- or U-shaped. In some embodiments, each C- or U-shaped opening has a width in the range of 0.5-1.5 mm, more preferably in the range of 0.6-1.2 mm.

In some embodiments, the or each opening is configured such that a portion of the separating element acts as a cover for the respective scoop when the scoop is in its first or non-sampling position. In certain embodiments, a separate cover may be arranged to cover one or more of the scoops when in the non-sampling position. In some embodiments, a separate cover may be arranged over each opening. In some embodiments, a single separate cover may be arranged over all openings.

As discussed in more detail below, in certain embodiments, the sampling device advantageously can be configured so as to minimise the disruption of the particulate matter in the sampling zone during insertion of the device into the particulate matter and collection of the sample. In this way, the sampling device enables the collection of samples which are accurately representative of the composition of the particulate matter at the sampling location.

In some embodiments, the particulate matter is a composite mixture containing two or more substances. In certain embodiments, the particulate matter is a pharmaceutical dry powder blend. However, it will be readily understood by those of ordinary skill in the art that the sampling device is not limited to use with pharmaceutical powders and can be used in conjunction with a wide variety of substances including agricultural products such as grains, food products, metal powders, dry mixed industrial chemical products and like applications.

In some embodiments, the particulate material is located in a container. The container may be in the form of a vat, mixing chamber, hopper or other such vessel. Preferably, the separating member is elongate. In some embodiments, the separating member length is substantially equal to the depth of the container. In other embodiments, the separating member length is substantially equal to the maximum depth of the particulate material within the container.

Preferably, the separating member has at least one sampling side and at least one non-sampling side, thereby to define and face towards the respective sampling and non-sampling zones adjacent or the respective sides.

In some embodiments, the separating member is in the form of a substantially open frame structure, wherein the separating member has a flat smooth sampling side surface with substantially no enclosed volume along the entire length of the sampling side of the separating member. The sampling side surface may be flat or planar, arcuate or curved, have first and second portions which extend at an angle relative to one another, or other suitable form. Advantageously, this configuration minimises the cross-sectional area of the separating member relative to the area of the sampling zone, thus minimising disturbance of the granule bed on the sampling side during insertion.

In some embodiments, the separating member includes at least one separating plate. In some embodiments, the or each plate is substantially flat, or has generally planar outer surfaces. In other embodiments, the or each plate may be angled, curved or otherwise profiled. Preferably, the sampling side surface is flat. In some embodiments, the sampling side surface may be polished, thereby to further inhibit disturbance of the granule bed in the area adjacent to the sampling side of the separating member during insertion into the granule bed.

In some embodiments, the separating member includes a plurality of separating plates arranged to form the open frame structure. In some embodiments, the separating plates include a plurality of vanes arranged to define the respective sampling and non-sampling sides. In some embodiments, the separating member includes a central hub, with each vane being fixed thereto and extending substantially radially outwardly from the central hub. Preferably, the vanes are substantially equal in thickness. In other embodiments, the vanes may have an irregular thickness. In some embodiments, the separating member may have a stiffening member configured to reduce bending of the separating member. In certain embodiments, one or more of the vanes of the separating may be configured to act as the stiffening member. In other embodiments, the stiffening member may be a separate element, or combination of two or more stiffening elements, adapted to stiffen the separating member.

In some embodiments, the separating member may include two, three, four, five or more vanes. The vanes are preferably substantially evenly spaced around the longitudinal axis or central hub of the separating member. For example, a separating member having three vanes would preferably be substantially Y-shaped in lateral cross section while a separating member having four vanes would preferably be substantially X-shaped in lateral cross section. In other embodiments, the vanes may be irregularly spaced around the longitudinal axis or central hub of the separating member.

In some embodiments, the cross-sectional profile of the separating member is substantially uniform along its length. In other embodiments, the cross-sectional profile of the separating member may vary along its length. Preferably, the separating member is tapered towards its operationally lower end. In some embodiments, the separating member is substantially axisymmetric or rotationally symmetric. In other embodiments the separating member may be asymmetrically shaped.

Advantageously, cross-section profiles such as angled, curved, Y-shaped or X-shaped provide a higher second moment of area than that of a flat plate with equivalent cross-sectional area, thus enabling a separating plate of adequate rigidity to be formed with a minimal lateral cross-sectional area. A smaller cross-sectional area advantageously minimises disturbance of the granule bed during insertion of the sampling device into the particulate matter and makes it easier to insert.

Preferably, the separating member includes at least one aperture extending between the sampling side and the non-sampling side and adapted to permit at least one sample capturing scoop to pass therethrough when moving between the sampling and non-sampling positions. Preferably, the number of apertures corresponds to the number of scoops. Preferably, the or each aperture is sized and shaped such that the or each scoop is close fittingly received therein.

Each aperture is preferably in the form of a slit. Preferably, the shape or profile of each slit substantially corresponds to a radial cross-section of at least a portion of the associated scoop. Preferably, the slit shape corresponds to a radial cross-section through one side edge of the scoop shell. In some embodiments, the slit is substantially C- or U-shaped. It will be appreciated that the slit is not limited to C- or U-shaped slits, rather the slits can correspond to the radial cross-sectional profile of any rotationally symmetrical scoop, which is intended to pass therethrough.

In particularly preferred embodiments employing 3 vanes in a Y-shaped cross-sectional profile, a first vane extends outwardly from the central hub in a first radial plane and a second and third vane each extends from the central hub in respective second and third planes parallel to a radial plane. Preferably, the second and third planes are each offset from radial planes by a predetermined distance. Preferably, the predetermined distance is equal to half the thickness of the first vane. Preferably, the first vane includes the aperture. Preferably, the included angle between each pair of adjacent vanes is substantially equal to 120°. Advantageously, this configuration provides a substantially flush alignment between an edge of the scoop and a surface of the vane when the scoop is in either the non-sampling or sampling position.

In some embodiments, at least one vane is adjustable to alter the position of the adjustable vane relative to an adjacent vane. Preferably, the adjustable vane is rotatably connected to the central hub of the separating member and rotatable to adjust the angle between the adjustable vane and an adjacent fixed vane. Preferably, the adjustable vane is adjacent to a sampling zone such that adjustment of the vane position alters the size of the sampling zone and the volume of the sample to be collected.

Preferably, the separating member is formed from a relatively rigid material such as, for example, steel. It will of course be appreciated that the separating member is not limited to steel and may be formed of any material with suitable rigidity, including other metals or plastics. Preferably, the material is selected and the cross-section of the separating member is configured to enhance its rigidity whilst minimising the cross-sectional area of the device.

In some embodiments, an operationally leading edge of at least one separating plate is bevelled on the non-sampling side. In other embodiments, the edge may be chamfered, filleted or otherwise sloped. Advantageously, the bevelled edge pushes particles into the non-sampling zone during insertion of the device to the particulate material, thus minimising disturbance of the sampling zone during insertion.

The separating member preferably includes a housing for a shaft. The housing may be configured to completely or partially enclose the shaft. Preferably, the housing allows the shaft to rotate substantially freely. In some embodiments, the housing is a substantially hollow tubular member.

The housing may be fastened to the separating member (for example, by welding or by other suitable fixation methods) or may be integrally formed with the separating member.

In some embodiments, the housing is located on a non-sampling side of the separating member. In other embodiments, a central hub of the separating member is configured to include the housing. Advantageously, this configuration increases the rigidity of the separating member.

In some embodiments, the separating member includes connecting formations for connecting a plurality of sampling devices together. Preferably, the devices are connected in parallel (that is, in a side-by-side configuration). Advantageously, connection of multiple devices side-by-side allows simultaneous collection of multiple samples from each desired sampling depth. In a preferred embodiment, three sampling devices are connectable to enable collecting of samples in triplicate. Preferably, the connecting formations are releasably connectable, thereby to enable connection and disconnection of two or more sampling devices as required.

In some embodiments, at least two lateral edges or vanes of the separating member include complementary connecting formations. In some embodiments, the connecting formations enable a snap-lock connection. Preferably, the connecting formations enable a sliding connection. In preferred embodiments, the connecting formations are in the form of a sliding joint. In one embodiment, the sliding joint includes complementary knob and claw formations on respective lateral edges or vanes of the separating member. The connecting formations may be in the form of an open channel with correspondingly shaped protrusion. The channel and protrusion may extend the full length of the separating member, or be positioned at discrete locations.

In some embodiments, at least one surface of the separating member is treated to reduce frictional resistance and disturbance of particles during insertion into the particulate matter. Preferably, at least one surface on the sampling side of the separating member is treated. More preferably, substantially all surfaces on the sampling side of the separating member are treated. In other embodiments, surfaces on both the sampling and non-sampling sides are treated. In some embodiments, the surface is polished. Preferably, the surface is electro-polished.

Preferably, the at least one sample scoop is hingedly connected to the separating member. Preferably, each scoop is configured for containing or enclosing a predetermined volume of particulate material.

Preferably, the or each scoop is located substantially within the sampling zone when in its sampling position and is located substantially within the non-sampling zone when in its non-sampling position. In other embodiments the or each scoop may be located partially within the sampling zone when in the sampling position. Preferably the or each scoop is located fully within the non-sampling zone when in non-sampling position.

Preferably, the or each scoop captures substantially undisturbed particulate material upon rotation from the non-sampling to the sampling position without the need for the captured particles to move. Preferably, the or each scoop captures a predetermined volume of the particulate material. Preferably, the or each scoop is configured to retain the captured sample as the device is withdrawn from the particulate matter. Preferably, the or each scoop is abuttingly engageable with a surface when in the sampling position to define a substantially closed cavity for capturing a sample of the particulate matter. Preferably, the or each scoop is releasably sealingly engageable with a surface of the separating member to form the substantially closed cavity.

In some embodiments, the sampling device includes a plurality of scoops. Preferably, the number of scoops corresponds to a predetermined number of samples for collection or to a predetermined number of sampling locations. In various embodiments, the sampling device may include one, two, three, four, five, six, seven, eight, nine, ten, eleven, twelve or more scoops.

In some embodiments, the scoops are arranged in spaced linear array along the length of the separating member. Preferably the scoops are arranged to each capture a sample of particulate material at a predetermined sampling depth. In other embodiments, the scoops are arranged in a spaced grid array along the length and width of the separating member. It will be understood that the invention is not limited to these particular exemplary forms and the scoops may be arranged in a variety of other configurations. In some embodiments, the scoops are regularly spaced. In other embodiments, the scoops may be irregularly spaced.

In some embodiments, the sample scoops are formed of steel. However, it will be appreciated that the scoops are not limited to steel and may be formed from any other material having suitable strength, stiffness and chemical inertness as required for the application.

In some embodiments, the axis of rotation of the scoops is substantially parallel to the longitudinal axis of the separating member. This configuration is advantageously simple to manufacture and operate. In other embodiments, the axis of rotation of the scoops is orthogonal to the longitudinal axis of the separating member. It will be appreciated that the invention is not limited to these exemplary configurations and that the axis of rotation of the scoops may be positioned at other angles and/or in other planes.

Preferably, the scoops have an outer shell and an internal cavity for capturing particulate matter therein. Preferably, the outer shell thickness is substantially uniform. In embodiments employing 316 or 316L stainless steel for pharmaceutical powder applications, a scoop shell thickness of 1 mm is preferred. However, the shell thickness may be adjusted depending on the material of the shell and/or the application to provide the shell with appropriate strength and stiffness for scooping the sample material.

In some embodiments, the scoop shells are substantially axisymmetric about their axis of rotation. In some embodiments, the scoop shells are substantially hemispherical. In other embodiments, each scoop shell may be spherical or semi-spherical, cylindrical or semi-cylindrical, capsule shaped, disc shaped, ellipsoid or semi-ellipsoid, spheroid or semi-spheroid or other appropriate axisymmetric shapes.

Advantageously, a scoop shell having an axisymmetric shape is able to rotate through the particulate matter to enclose the particulate matter without significant movement or disruption of the particles.

In some embodiments, the shape of the scoop shell substantially corresponds with the shape of the swept area defined by the range of movement of the leading edge of the scoop.

In some embodiments, each scoop is a single integrally formed component. In other embodiments, the scoops may be formed from a plurality of segments.

Preferably, the leading edge of each scoop is bevelled, chamfered, filleted or otherwise sloped on the non-sampling side. Advantageously, the bevelled edge pushes particles away from the internal cavity of the scoop as the scoop rotates through the particulate material, thus minimising disturbance of the particles to be captured during rotation of the scoop.

Preferably, the sampling device includes a rotation mechanism for rotating the at least one scoop relative to the separating member. Preferably, the rotation mechanism includes a shaft. The shaft is preferably axially rotatably mountable to the separating member and engageable with the at least one scoop to rotate the scoop.

Preferably, the or each scoop includes engaging formations adapted to facilitate engagement with the rotation mechanism for selectively driving rotation of the scoops between the sampling and non-sampling positions. Preferably, each scoop is releasably engageable with the rotation mechanism (for example, a shaft). Preferably, each engaging formation is in the form of an aperture. Preferably, the aperture is substantially aligned with the axis of rotation of the scoop. In some embodiments, the aperture has a cross-sectional profile substantially corresponding to a cross-sectional profile of a shaft. In other embodiments, the aperture may include a keyway for receiving a key for engagement with a correspondingly keyed shaft.

In some embodiments, the scoops are interchangeable. Preferably, the scoops are selectable from a range of sizes, shapes, volumes, materials and/or shell thicknesses. Interchangeable and/or selectable scoops advantageously renders the sampling device readily adaptable for use in collecting various sample sized or with various types of particulate matter.

In some embodiments, the axis of rotation of the shaft is substantially parallel with axis of the sampling device. Preferably, the axis of rotation is coaxially aligned with the axis of the sampling device. In some embodiments, the shaft is engageable with the scoop for conjoined coaxial rotation therewith. In other embodiments, the shaft is engageable with the scoops for non-coaxial rotation. For example, in one embodiment, the axis of rotation of the at least one scoop is orthogonal to the axis of rotation of the shaft. It will be appreciated that the invention is not limited to these exemplary configurations and that the axis of rotation of the shaft may be positioned at other angles and/or in other planes relative to the sampling device and/or axis of scoop rotation.

Preferably, the length of each vane of the separating member is greater than the (maximum) radius of the swept area of each scoop. In some embodiments, the length of each vane is at least 1.25 times greater than the radius of the swept area of each scoop. In some embodiments, the length of each vane may be at least 1.5, 1.75, 2.0, 2.5, 3.0 times greater than the radius of the swept area of each scoop. The provision of vanes having a greater length than the radius of the swept area advantageously assists in forming an open frame structure for the sampling device. Such an open frame structure, in combination with the ability to ensure that no part of a scoop is on the sampling side (or within the sampling zone) upon insertion into a reservoir of particulate material, provides the device with a relatively small footprint and adds resistance to any side movement, thereby to substantially inhibit or minimise any disturbance of the particulate material and thus resulting in more accurate and repeatable sampling results.

In some embodiments, the shaft is removably mounted to the separating member. Preferably, the shaft extends substantially the length of the separating member. Preferably, the shaft extends beyond the separating member at its operatively upper end to enable engagement with a driving mechanism, locking mechanism and/or to define a handle.

Preferably, the shaft is in the form of an elongate rod or tube. In some embodiments, the cross-sectional profile of the shaft is substantially uniform along its length. In some embodiments, the cross-sectional profile of the shaft is substantially square, more preferably square with rounded corners. Such embodiments advantageously provides a snug, yet freely rotatably fit within a tubular housing of the separating member. In other embodiments, the cross-sectional profile of the shaft may be rectangular, triangular, polygonal, hexagonal or any other suitable cross-sectional shape for transmitting torque to rotate the sample scoops. Preferably, the cross-sectional profile of the shaft is complementary to an aperture on the at least one scoop adapted for receiving the shaft.

In still other embodiments, the cross-sectional profile of the shaft may vary along its length. In such embodiments the shaft may include engaging formations, such as splines or a keyway and key for engaging complementary formations for transmitting torque to rotate the sample scoops. The shaft cross section may be substantially round.

Preferably, the shaft material and cross-sectional area are configured to provide sufficient stiffness and strength to substantially resist deformation due to torsion and/or bending forces exerted on the shaft during operation of the sampling device.

Preferably, the rotation mechanism further includes a driving mechanism for rotating the shaft. In some embodiments, the driving mechanism is in the form of a lever arm connected to the shaft at its operatively upper end. Preferably, the lever is movable to rotate the shaft and thus rotate the sample scoops from the non-sampling position into the sampling position.

In certain embodiments, the lever arm is perpendicular to the shaft. In embodiments employing a flat plate, the lever arm length is preferably half the width of the sampling device. In embodiments employing a plurality of radially extending vanes, the lever arm length is preferably substantially equal to the width of one vane. The lever arm preferably includes a flared end portion to accommodate a user's grip.

In some embodiments, the rotation mechanism is operable using manual driving force. In other embodiments the rotation mechanism is operatively associated with an actuator, such as an electric motor. It should be appreciated, however, that alternative sources of motive power may be used, including electric, hydraulic or pneumatic motors.

Preferably, the lever arm includes at least a portion made from ferromagnetic material for facilitating engagement with a magnetic locking mechanism.

Preferably, the sampling device further includes a releasable locking mechanism to selectively lock the scoops relative to the separating member. Preferably, the locking mechanism selectively prevents rotation of rotation mechanism thereby to lock the scoops. Preferably, the locking mechanism is adapted to lock the scoops in at least the sampling position. In some embodiments, the locking mechanism is adapted to lock the scoops in either of the sampling or non-sampling positions.

In some embodiments, the locking mechanism is adjustable to allow adjustment of the locking positions and locking force.

Preferably, the locking mechanism is in the form of a restraining member for substantially preventing movement of the lever arm. In some embodiments, the restraining member is in the form of a hook, channel or groove configured to receive the lever arm to prevent rotation. In other embodiments, the restraining member includes a spring system, the spring system acting to bias the lever arm towards the sampling position and/or non-sampling position. In other embodiments, the locking mechanism includes at least one magnetic lock for magnetically restraining the lever arm. In certain embodiments, the locking mechanism includes a pair of magnetic locks for magnetically restraining the lever arm to position the scoops in the sampling and non-sampling positions, respectively. It will be understood that the invention is not limited to these particular exemplary forms of control and locking mechanisms. For example, the control and locking mechanisms may not be an integral part of the sampling device, rather such mechanism could be a releasably detachable unit or units that can be employed as required.

Preferably, the sampling device includes a handle at its proximal end. The handle is preferably adapted to facilitate insertion (and withdrawal) of the sampling device to the particulate material. In certain embodiments, the handle is shovel handle shaped (e.g. generally "D" shaped). In other embodiments, the handle is mushroom shaped. It will be understood that the invention is not limited to these particular exemplary forms of handles, and may employ handles of various other shapes.

Preferably, the components of the sampling device are manufactured from grade 316 or grade 316L stainless steel. However, it should be appreciated that the sampling device is not limited to steel and may be constructed from any material with suitable mechanical strength and chemical inertness as appropriate for the application including metals or plastics such as aluminium, titanium, delrin, PTFE, or other suitable materials.

According to another aspect of the invention, there is provided a sampling device, including:
- an elongate separating member having a sampling side and a non-sampling side, the elongate member having one or more through openings extending from the sampling side to the non-sampling side, the separating member being adapted for insertion into a reservoir of particulate material, thereby to define a sampling zone and a non-sampling zone within the reservoir;
- a shaft operably associated with the separating member, the shaft being positioned away from the sampling side and selectively rotatable about its longitudinal axis; and
- one or more sample capturing scoops attached to the shaft so as to be aligned with a respective one of the openings;
- wherein rotation of the shaft about its longitudinal axis causes a corresponding rotation of the or each scoop between a first position (the non-sampling position) the scoop is on the non-sampling side of the separating member such that sampling side of the separating member is free of protuberances during insertion into the reservoir, and a second position (the sampling position) in which the scoop is positioned on the sampling side of the separating member, thereby to enclose the sample of particulate material upon rotation of the scoop towards the second (sampling) position.

According to another aspect of the invention, there is provided a sampling device, including:
- an elongate separating member having a sampling side and a non-sampling side, the elongate member having at least one through opening extending from the sampling side to the non-sampling side; and
- at least one sample capturing scoop, the scoop being selectively rotatable relative to the separating member between a first position in which the scoop is located on the non-sampling side such that there are no protrusions on the sampling side, and a second position in which the scoop is located on the sampling side for collecting a sample of a powdered material, in use.

According to another aspect of the present invention there is provided a sampling device for capturing a sample of particulate material, the device including:
- a separating member for insertion into the particulate material to define at least one sampling zone and at least one non-sampling zone; and
- at least one sample capturing scoop connected to the separating member and rotatable between a non-sampling position and a sampling position such that a sample is captured from substantially undisturbed particulate material in the sampling zone.

According to another aspect of the present invention there is provided a method for capturing a sample of particulate material using the device of the first aspect of the invention including the steps of:
a) rotating the at least one scoop out of the sampling position;
b) at least partially inserting the separating member into the particulate material to define at least one sampling zone and at least one non-sampling zone; and
c) rotating the at least one scoop from the non-sampling position to the sampling position thereby to capture a sample of substantially undisturbed particulate material in the sampling zone.

BRIEF DESCRIPTION OF THE DRAWINGS

Preferred embodiments of the invention will now be described, by way of example only, with reference to the accompanying drawings in which:

FIG. 10a shows a side view of the sampling device of FIG. 8;

FIG. 10b shows a cross-sectional view of the sampling device of FIG. 10a taken along line B-B shown with a scoop in the non-sampling position;

FIG. 10c shows a cross-sectional view of the sampling device of FIG. 10a taken along line B-B shown with a scoop in the sampling position having captured a sample of particulate material;

FIG. 10d shows a side view of the sampling device of FIG. 8 with an additional cover to protect the scoops during insertion;

FIG. 10e shows a cross-sectional view of the sampling device of FIG. 10d taken along line C-C shown;

FIGS. 11a and 11b show cross-sectional views of a fifth embodiment of a sampling device according to the present invention showing a scoop in the non-sampling and sampling positions, respectively;

FIGS. 12a and 12b show cross-sectional views of a sixth embodiment of a sampling device according to the present invention showing a scoop in the non-sampling and sampling positions, respectively;

FIG. 13 shows a perspective view of a seventh embodiment of a sampling device according to the present invention;

FIG. 14 shows a perspective view of an eighth embodiment of a sampling device according to the present invention;

FIGS. 15a to 15d show perspective views of interchangeable inserts of a ninth embodiment of a sampling device according to the present invention;

FIG. 16 shows a cross-sectional view of a tenth embodiment of a sampling device according to the present invention; and FIG. 17 shows an enlarged cross-sectional view of the sampling device of FIG. 1 showing the scoop in the non-sampling position.

PREFERRED EMBODIMENTS OF THE INVENTION

Figure 1:
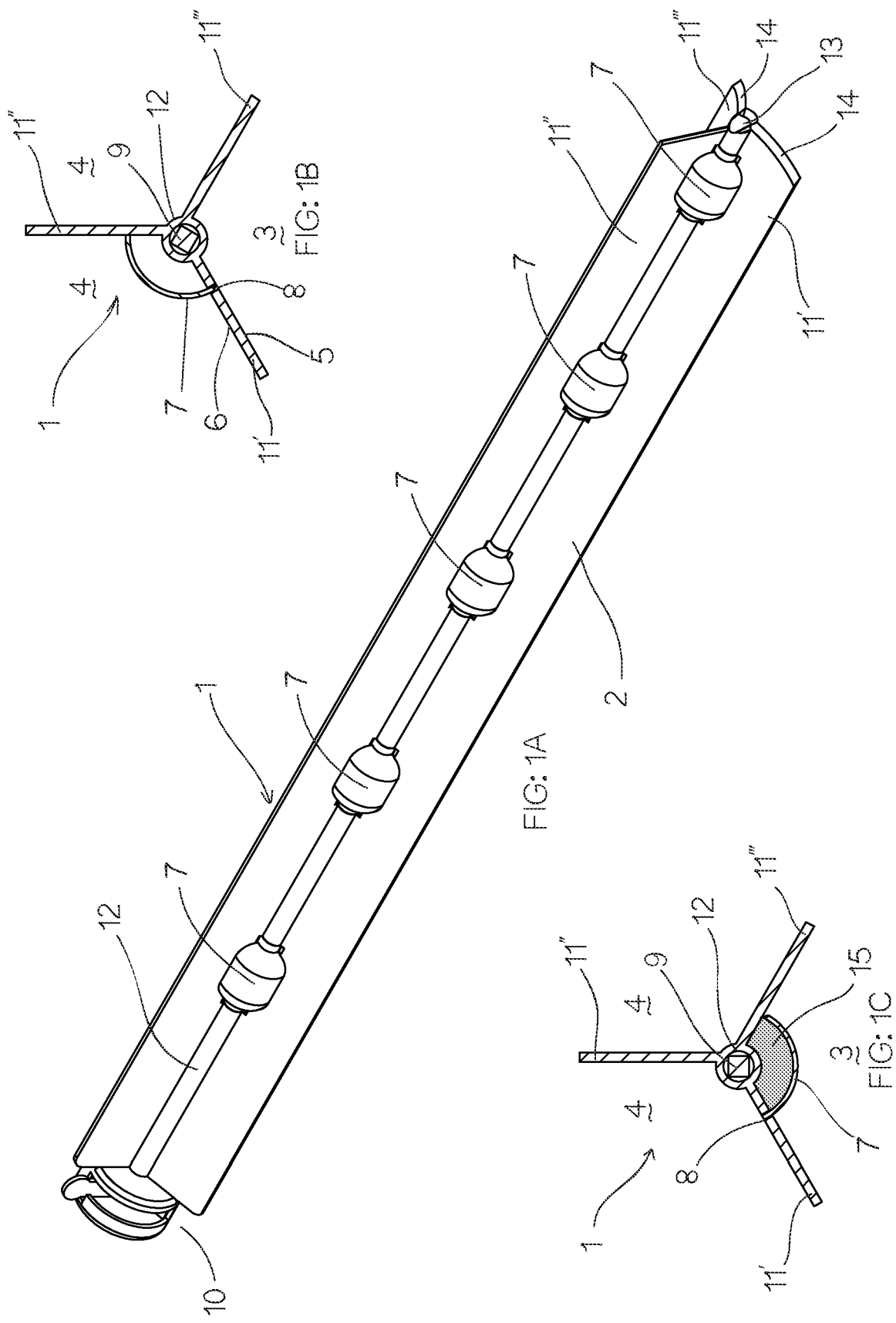
FIG. 1a shows a perspective view of a first embodiment of a sampling device according to the present invention.
FIG. 1b shows a cross-sectional view of the sampling device of FIG. 1 showing the scoop in the non-sampling position.
FIG. 1c shows a cross-sectional view of the sampling device of FIG. 1 showing a scoop in the sampling position having captured a sample of particulate material.
Figure 2:
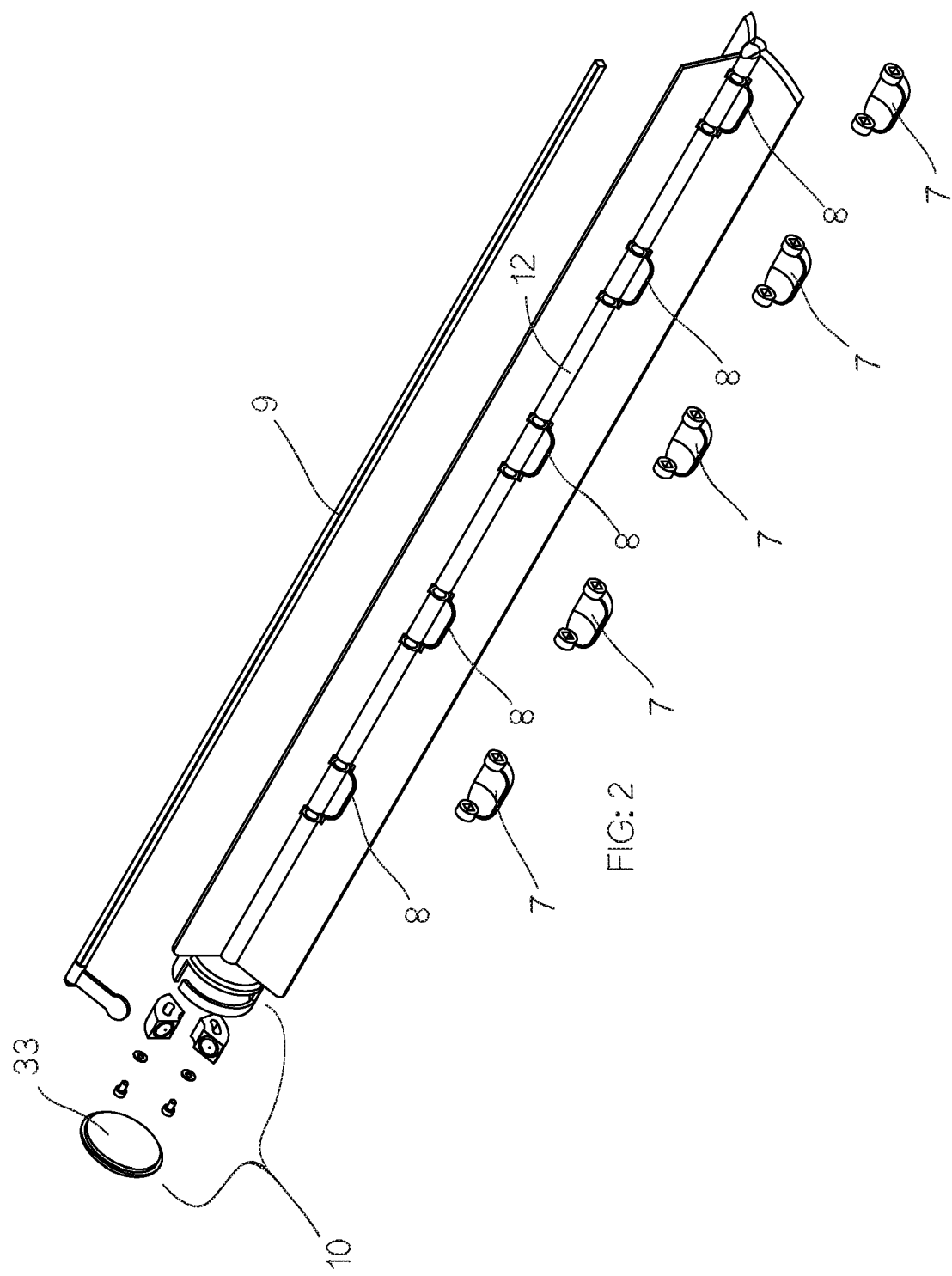
FIG. 2 shows an exploded view of the sampling device of FIG. 1.

Referring initially to FIGS. 1A to 1C, the invention provides a sampling device 1 for capturing a sample of particulate material.

In the illustrated embodiments, the device 1 is adapted for capturing a sample of a predetermined volume of a pharmaceutical powder blend from a reservoir of the particulate material housed within a mixing vessel. For clarity of description and by way of example only, the following description of the drawings is made with specific references to pharmaceutical powders, where it is desired to test the ratios of the various constitute components that form a particular pharmaceutical. However, it will be appreciated by those skilled in the art that the sampling device is not limited to use with pharmaceutical powders but is readily adaptable for use in sampling other forms of blended particulate material where it is desired to accurately test the ratios of the various component materials in a sample against the desired ratios of a particular blended substance.

In the illustrated embodiment, the sampling device 1 has an elongate separating member 2 that is configured for insertion into the particulate material to define at least one sampling zone 3 and at least one non-sampling zone 4, as shown in FIG. 1B. The separating member has a sampling side 5 and non-sampling side 6 adjacent the respective sampling and non-sampling zones.

The sampling device 1 includes a plurality of scoops 7 hingedly connected to the separating member 2. The scoops 7 are rotatable through apertures in the form of slits or through openings 8 in the separating member 2 to move from a non-sampling position in the non-sampling zone 4, as shown in FIG. 1B, into a sampling position in the sampling zone 3, as shown in FIG. 1C.

Referring to FIG. 1B, it can be seen that, when the scoops are in the non-sampling position, no part of the scoops is located on the sampling side of the separating member. That is, in the non-sampling position, the scoops are outside of the sampling zone and project away from the non-sampling side surface of the separating member. By positioning the scoops entirely on the non-sampling side of the separating member, there is advantageously no projection associated with the sampling side that may undesirably disturb the reservoir of particulate material during insertion of the separating member into the particulate material. In the embodiment of FIG. 1B, the sampling side surface of the separating member is generally v- or Λ-shaped with two flat smooth surfaces extending at an angle relative to one another. This flat smooth surface of the sampling side surface advantageously ensures that there is only relative minor, if any, disturbance to the reservoir of particulate material within the sampling zone. It will be appreciated that by ensuring such minor or no disturbance enables the present sampling device 1 to obtain samples of the particulate material which accurately reflect the composition of the particulate material within the reservoir, particularly the ratios of the various materials which form the blended particulate material at the location at which the sample is taken.

The sampling device 1 also includes a shaft 9 engageable with the scoops 7 to rotate the scoops relative to the separating member, and an operational control mechanism 10 including a locking mechanism 21 for selectively locking the scoops 7 against rotation.

In the embodiment of FIG. 1, the separating member includes three vanes 11 extending substantially radially outwardly from a tubular central hub 12. The vanes are substantially evenly circumferentially spaced around the central hub, such that the included angle θ between each adjacent pair of vanes is 120°, as shown in FIG. 17. The vanes separate the particulate matter to form one sampling zone 3 and two non-sampling zones 4. The vanes 11 are substantially planar and each extends along the length of the separating member 2.

The separating member is tapered towards its operationally lower end 13. In addition, the two vanes 11 adjacent the sampling zone 3 include a bevelled leading edge 14 at the operationally lower end of their non-sampling sides. The tapering and bevelled edges advantageously minimise the force required for insertion into the particulate material and also direct any disturbance of the granule bed during insertion towards the non-sampling zone 4, leaving the granule bed in the sampling zone 3 substantially undisturbed.

As can be seen in FIG. 1B, no part of any scoop is within the sampling zone when the scoops 7 are in the non-sampling position. Thus, the separating member 2 advantageously has substantially no protrusions on the surfaces adjacent the sampling zone 3, thereby minimising disturbance of the granule bed during insertion of the device 1 into the particulate matter.

Further, as illustrated in FIG. 17, a first vane 11' extends from the central hub 12 along a radial plane, while the second 11" and third 11'" vanes extend in respective planes which are parallel to radial planes and offset by a distance X equal to half the thickness of the first vane 11'. This configuration advantageously provides a substantially flush alignment between the operationally leading edge 17 of the scoops 7 and the surface of the first vane 11' adjacent the sampling zone 3 when the scoops 7 are in the non-sampling position, as shown in FIG. 17. This advantageously closes the opening of the slit, further aiding the provision of a substantially planar surface to the first vane and preventing flow of the particulate material into the slits, thereby reducing the disturbance of the particulate material. Additionally, this configuration advantageously minimises the quantity of particles which may become trapped in the slits 8 during insertion of the separating member 2 into the particulate material.

The embodiment of FIG. 1 has five sample capturing scoops 7 arranged in an evenly spaced linear array along the length of the separating member 2. Other embodiments may have fewer or more scoops, which may be arranged in a linear or grid array, or irregularly on the separating member 2. Advantageously, a plurality of scoops in spaced array allows for a series samples to be collected simultaneously at preselected sampling depths corresponding to the spacing of the scoops 7.

Each scoop 7 is rotatable from the non-sampling position to the sampling position to capture a predetermined volume of the particulate material. As can be seen in FIG. 1C, when in the sampling position, the scoops 7 are releasably sealingly engaged with a sampling side surface of the separating member 2 adjacent the sampling zone 3 to form a substantially closed cavity 15 containing a sample of particulate material.

Figure 3:
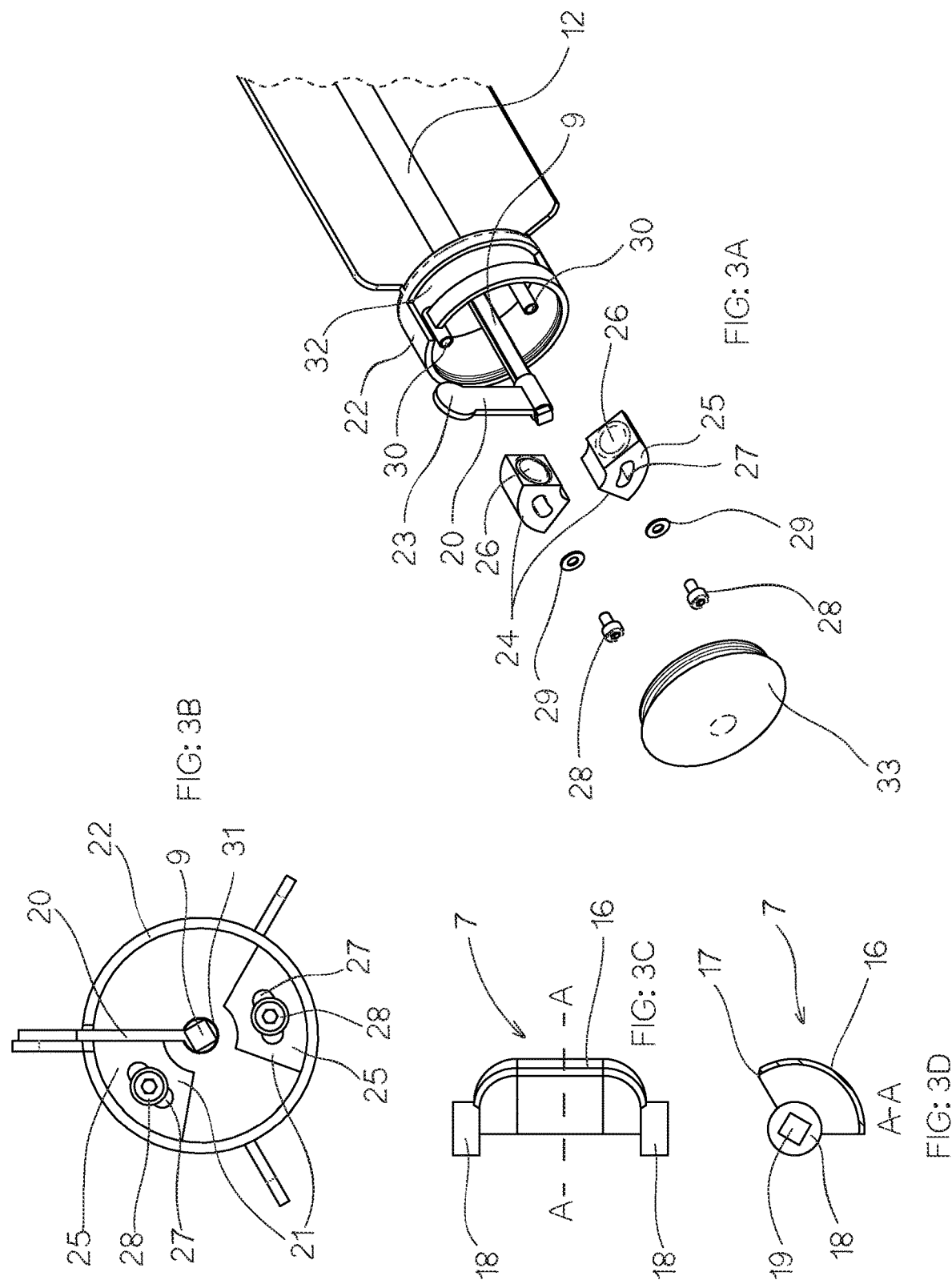
FIG. 3a shows an exploded view of the proximal end of the sampling device of FIG. 1 showing the lever arm and locking mechanism.
FIG. 3b shows an end view of the operationally upper end of the sampling device of FIG. 1.
FIG. 3c shows a side view of a sample collection scoop of the sampling device of FIG. 1.
FIG. 3d shows an end view of the sample collection scoop of FIG. 3c taken along line A-A.

Referring to FIGS. 3C and 3D, each scoop has a shell 16 surrounding an inner cavity for containing a sample of the particulate material. The shell 16 of each scoop is axisymmetric about the axis of rotation of the scoop. In the illustrated embodiment, each scoop shell 16 is semi-cylindrical with rounded end portions. Each scoop has a bevelled leading edge 17 on the outer surface of the shell. This allows the scoop to rotate through the particulate material in the sampling zone 3 to substantially enclose a sample of the particulate material without disturbing the granule bed of the sample. The bevelled edges 17 of the scoops also advantageously assist in clearing any fine powder which may have been trapped in the slits 8 of the separating member 2 during insertion to the particulate material. The provision of scoops which can be rotated from a non-sampling side of the device to a sampling side of the device in a manner which encloses the desired sample volume of particulate material is particularly advantageous as it does not require any flow or other movement of the particulate material, rather it is the movement of the scoop which encapsulates the sample to be tested. In this way, the reservoir of particulate material is generally not disturbed by the action of the sampling device, thereby to enable a sample to be taken which accurately reflects the composition of the blended particulate material within the reservoir at the location at which the sample is taken.

The scoops 7 are each hingedly connected to the separating member 2 via a pair of engaging formations 18. The engaging formations 18 are substantially cylindrical and coaxial with the axis of rotation of the scoops 7. The outer diameter of the engaging formations 18 is substantially equal to the outer diameter of the central hub 12 of the separating member 2. The engaging formations are insertable to the separating member 2 at cut-out portions 8' where the apertures 8 extend into the central hub 12. When inserted, the engaging formations are substantially coaxially aligned and flush with the central hub.

In the illustrated embodiment, each engaging formation 18 has a central aperture 19 having a substantially square cross-section extending axially therethrough for engagement with the shaft 9, whereby rotation of the shaft causes a corresponding rotation of the or each scoop connected thereto.

The shaft 9 is insertable to the central hub 12 of the separating member 2, which forms a housing for the shaft, and through the apertures 19 of the scoops 7. The cross-sectional shape of the shaft 9 is square, preferably with rounded corners. This shape advantageously allows the shaft 9 to rotate within the tubular central hub 12, while engaging the correspondingly substantially square shaped apertures 19 of the scoops 7 for conjoined rotation therewith.

In other embodiments, the rotational axis of the scoops is not aligned with that of the shaft. For example, the embodiment illustrated in FIG. 13 has a scoop rotatable along an axis orthogonal to the shaft.

The shaft 9 extends along the length of the separating member 2. The shaft 9 extends beyond the separating member 2 at its operationally upper end to engage with a driving mechanism in the form of a lever arm 20 and the locking mechanism 21 in the form of magnetic locks 24 within control housing shell 22, as shown in FIG. 3A.

Referring to FIG. 3A, the lever arm 20 is welded to the upper end of the shaft 9 and extends substantially perpendicularly therefrom. A flared portion 23 is provided to accommodate a user's grip. The lever arm 20 is rotatable to effect corresponding movement of the shaft 9 and scoops 7 between the non-sampling and sampling position.

In the embodiment of FIG. 3B, the locking mechanism 21 includes a pair of adjustable magnetic locks 24 for magnetically restraining the lever arm 20. The lever arm includes a portion made from a ferromagnetic material for engagement with the magnetic locks 24. The locks 24 are positioned to selectively restrain the lever arm 20 (and thus the shaft 9 and scoops 7) in either the non-sampling or sampling position.

Each adjustable magnetic lock 24 includes a body 25 and a magnet 26 fixed to the body. A slot 27 extends through the body to allow adjustable mounting to the control housing shell 22 by screws 28 and washers 29. Each lock position may be adjusted by sliding the lock body 25 along the path of slots 27 and fixed in the desired position by tightening screw 28. Advantageously, this allows adjustment of the sampling position of the scoops 7 to ensure tight closure against the separating member 2.

The control housing shell 22 is configured to enclose the magnetic locking mechanism 21 and partially enclose the lever arm 20. A pair of threaded mounting posts 30 are provided for to receive screws 28 for mounting the adjustable magnetic locks 24. The control housing shell has a central aperture 31 to allow insertion of the shaft 9, and a slot 32 to allow insertion and rotation of the lever arm 20. The sampling device further includes a handle 33 in the form of a threaded cap, engageable with a threaded portion of the control housing shell.

The embodiment of FIG. 1 is assembled prior to use in the following sequence. When all the parts are clean, the user places the engaging formations 18 of each sample capturing scoop 7 into cut-out portions 8' in the central hub 12 in between the first vane 11' and second vane 11" with the bevelled edge 17 of the scoop 7 resting in the corresponding slit 8. Once all scoops have been positioned, the shaft 9 is inserted through aperture 31 into the central hub 12 and through the apertures 19 in the engaging formations on the scoops 7. The handle cap 33 is then screwed into the control housing shell 22 to secure the lever arm 20 and shaft 9 in position for operation.

In use, the lever arm 20 is rotated to position the scoops 7 in the non-sampling position and locked by one of the magnetic locks 24. The separating member 2 is then inserted substantially vertically into the reservoir of the particulate material. Once the desired sampling position or depth has been reached, force is applied to the lever arm 20 to separate the lever arm from the lock 24 and rotate the arm into locking engagement with the other lock. This rotates the scoops 7 from the non-sampling position to the sampling position, capturing a sample of the particulate material in each scoop. Once the samples have been captured, the separating member is withdrawn from the particulate material. Any residual particles on the exterior of the sampling device 1 may be brushed or shaken off. The device 1 may then be positioned over individual sample collection containers, and the lever arm 20 rotated back into the non-sampling position, thereby to release the samples from the scoops 7 and into the containers for subsequent analysis. The sampling device 1 may then be dismantled for cleaning.

Figure 4:
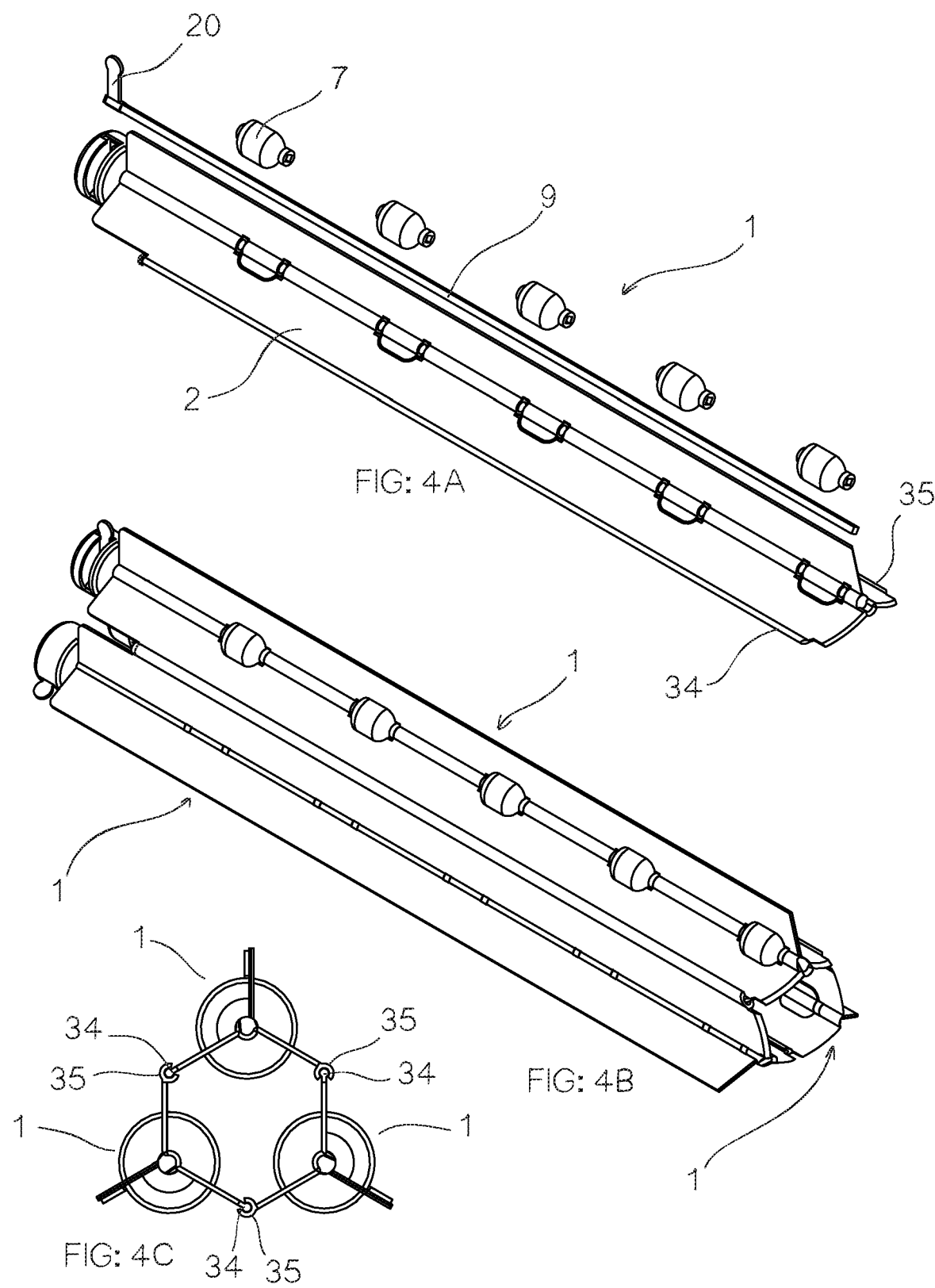
FIG. 4a shows an exploded view of a second embodiment of a sampling device according to the present invention.
FIG. 4b shows a perspective view of three of the devices of FIG. 4 joined together.
FIG. 4c shows an end view of the devices of FIG. 4b.

Referring to FIG. 4, in some embodiments, the sampling device 1 includes connecting formations in the form of a knob 34 and claw 35 connectable to make a sliding joint. As shown in FIG. 4C, in a three-vane sampling device, the connecting formations allow connection of three devices in a side-by-side ring arrangement. Each device 1 preferably has an array of scoops 7 in identically spaced array. This advantageously allows simultaneous collection of multiple samples at each sampling depth. In the illustrated embodiment, samples are collected in triplicate at each sampling depth.

Figure 5:
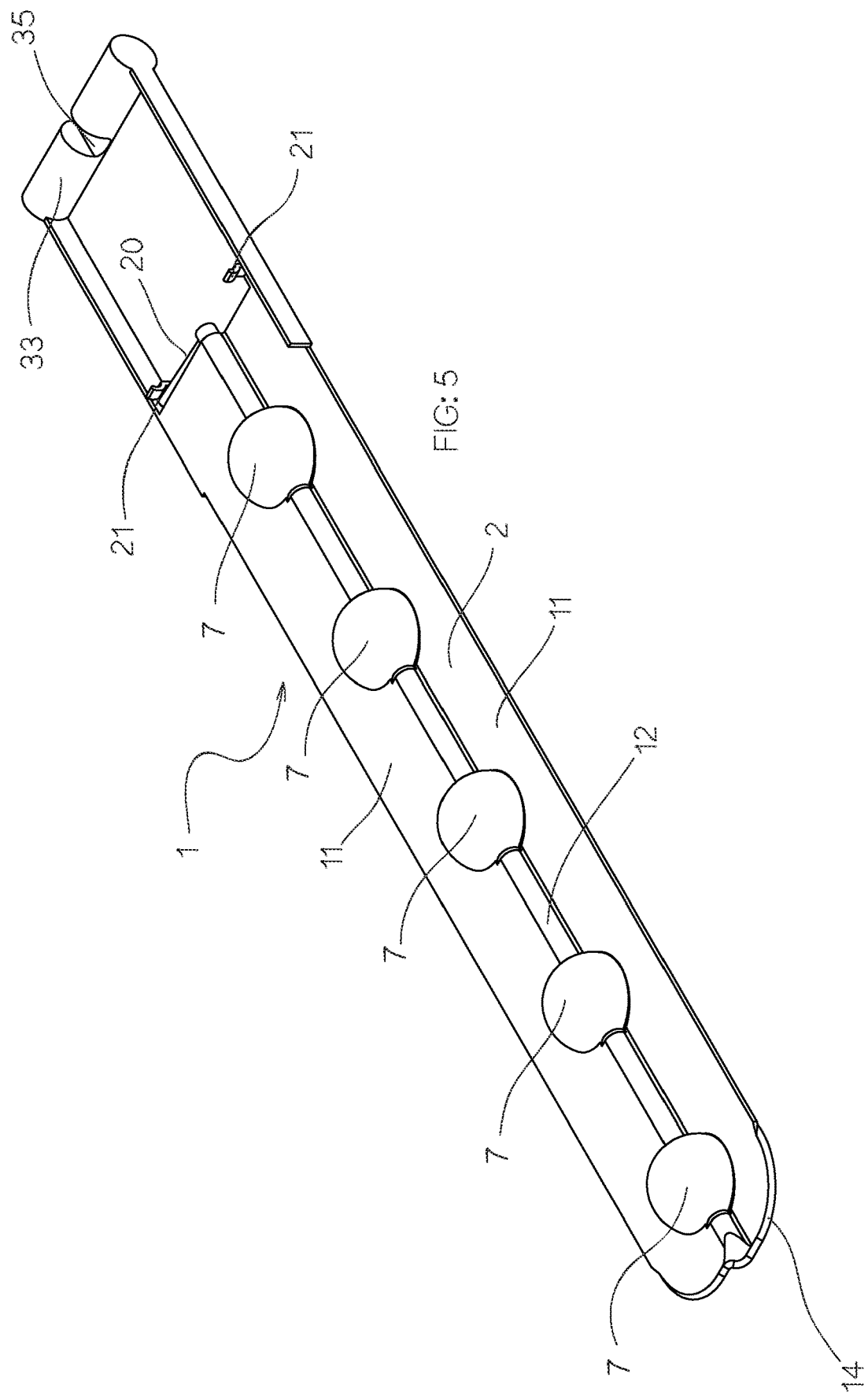
FIG. 5 shows a perspective view of a third embodiment of a sampling device according to the present invention.
Figure 6:
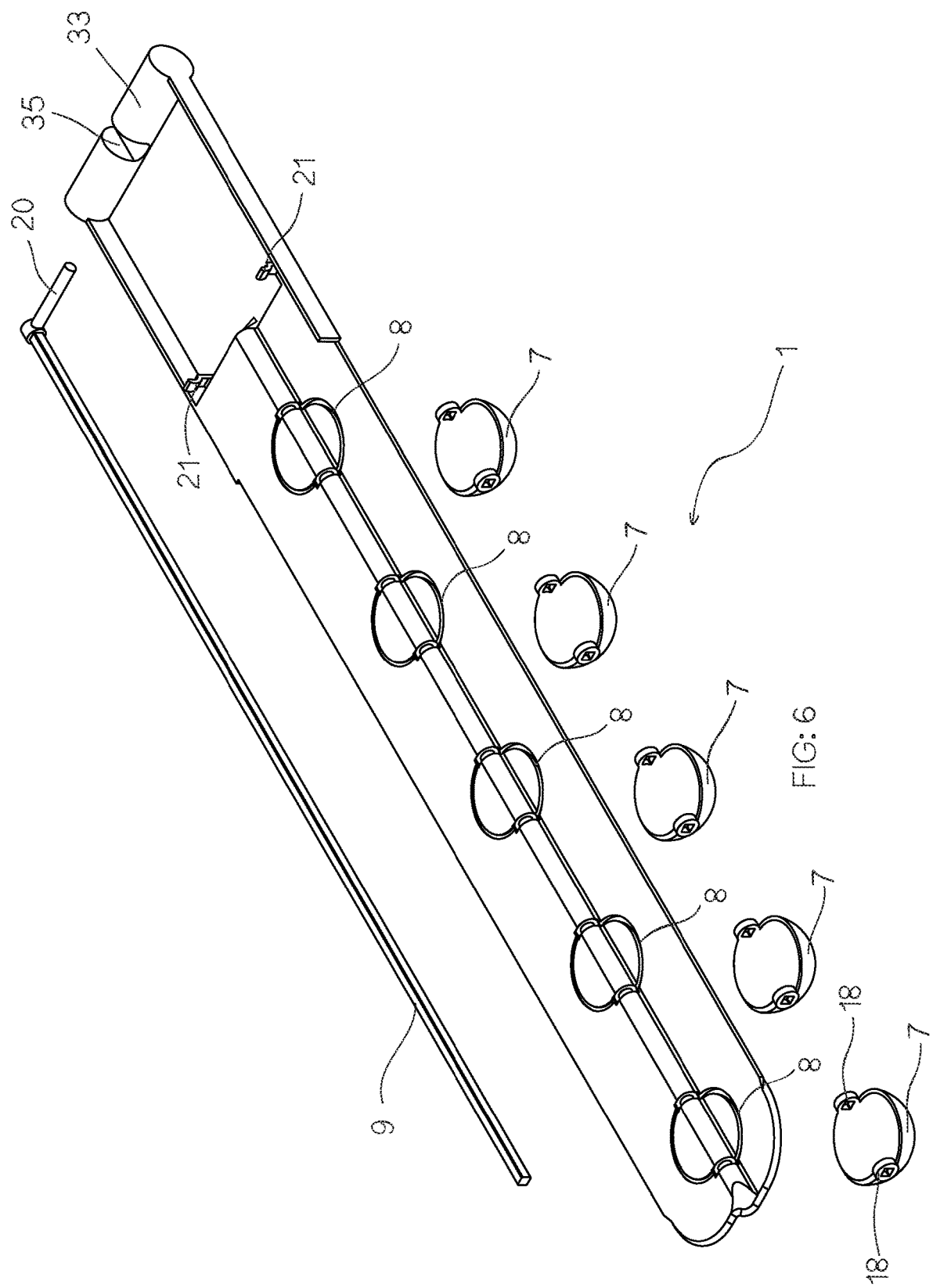
FIG. 6 shows an exploded view of the sampling device of FIG. 5.
Figure 7:
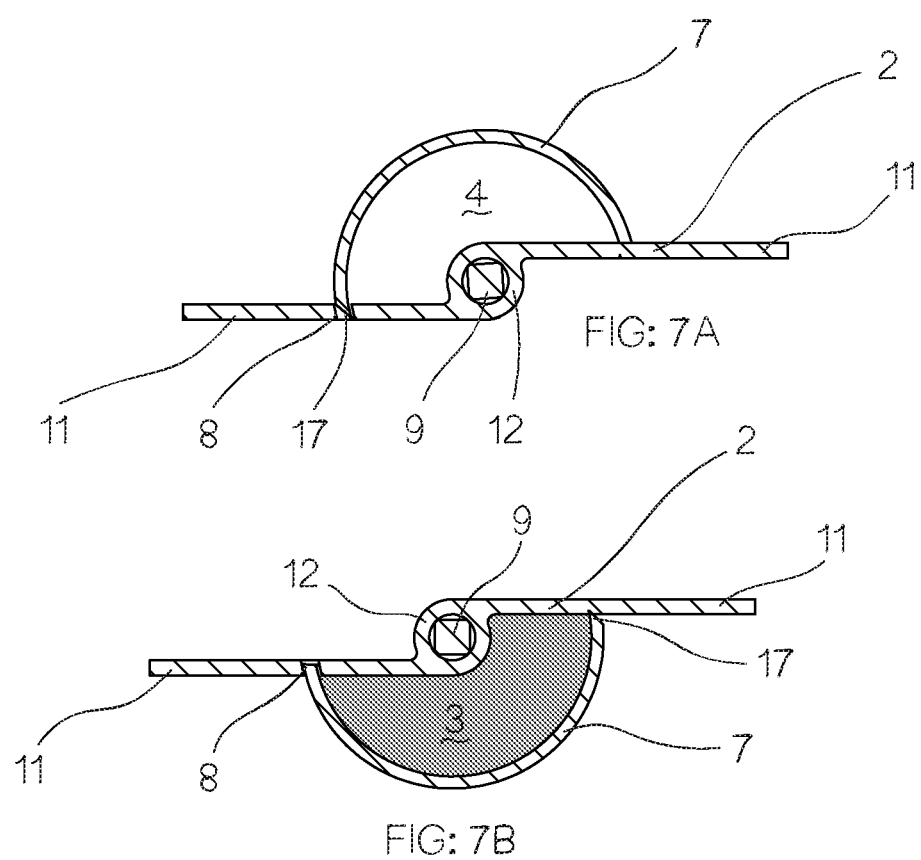
FIG. 7a shows a cross-sectional view of the sampling device of FIG. 5 shown with the sample collecting scoop in the non-sampling position.
FIG. 7b shows a cross-sectional view of the sampling device of FIG. 5 shown with a sample collecting scoop in the sampling position having captured a sample of particulate material.

FIGS. 5 to 7 illustrate an alternative embodiment having a separating member including two vanes 11 extending from central hub 12. The two vanes extend generally parallel to one another and are offset from the central longitudinal axis of the hub or shaft by a predetermined distance. In this embodiment, the scoops 7 have substantially hemispherical shaped shells.

The locking mechanism 21 of the embodiment of FIGS. 5 to 7 is in the form of a pair of catch or latch elements for releasably retaining the lever arm in either the sampling or non-sampling position.

The handle 33 is in the form of a bar grip, fixedly connected to the separating member 2. A central recess 35 in the handle allows insertion and retraction of the shaft 9 and lever arm 20 to the central hub 12.

The scoops are rotatable from the non-sampling side to the sampling side as shown in FIGS. 7A and 7B, respectively. In the illustrated embodiment it can be seen that the edges of the scoops 7 do not align perfectly with the faces of the separating member 2 when positioned in the slits 8. However, the bevelled leading edge 17 of the scoops 7 serves to direct any powder entrapped in the slits towards the outside of the scoop such that it does not disturb, or form part of, the captured sample.

Figure 8:
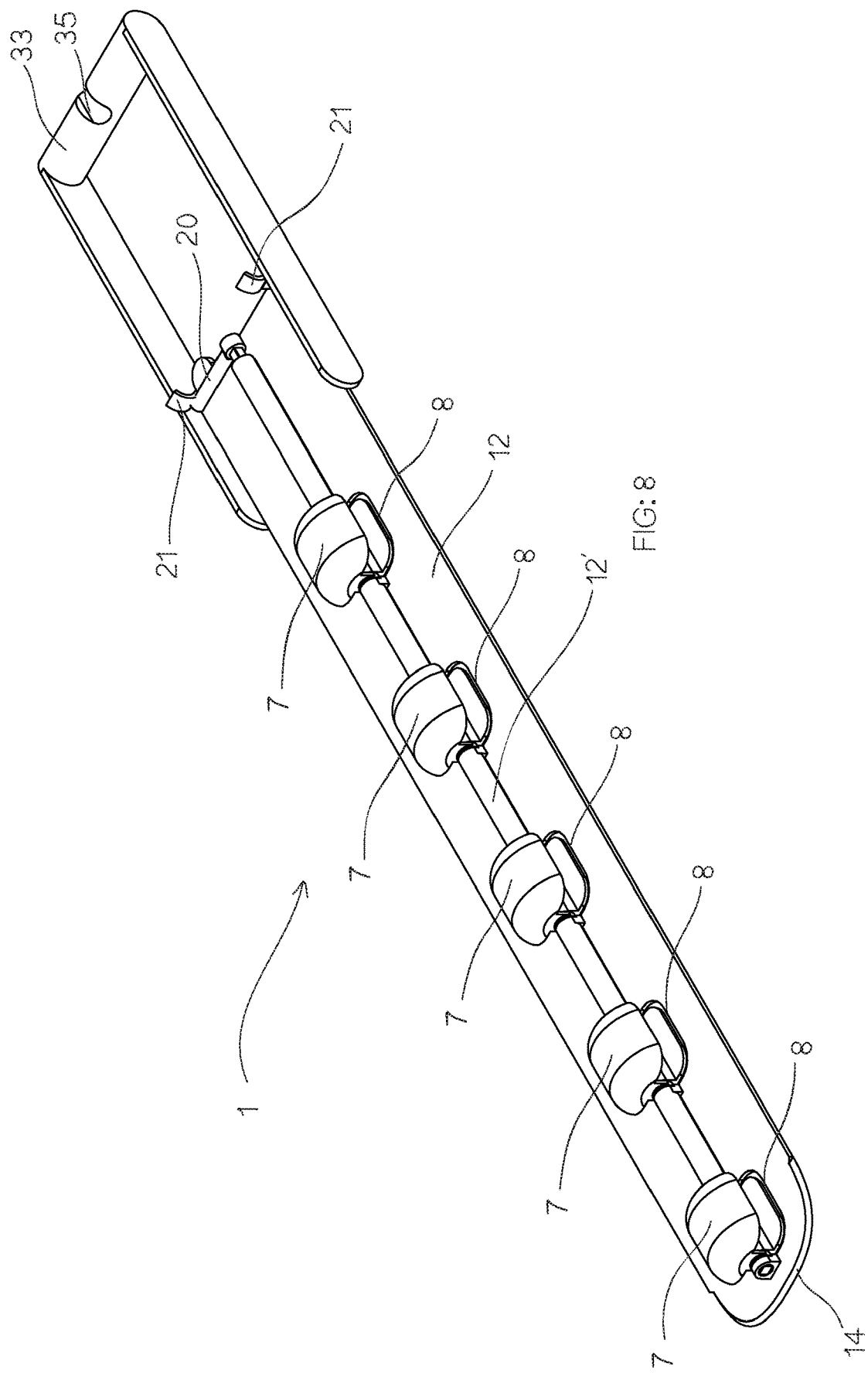
FIG. 8 shows a perspective view of a fourth embodiment of a sampling device according to the present invention.
Figure 9:
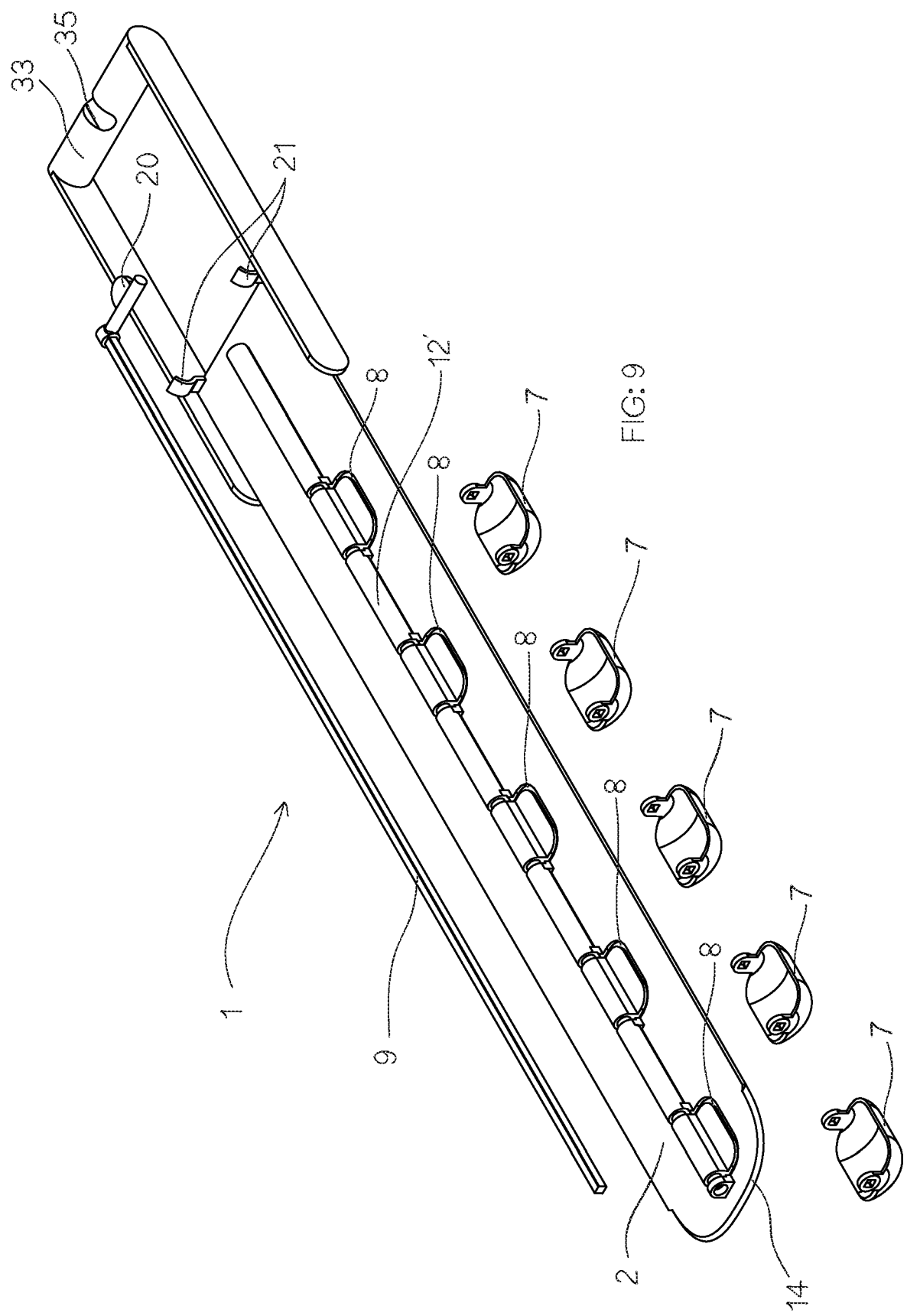
FIG. 9 shows an exploded view of the sampling device of FIG. 8.

FIGS. 8 to 10 illustrate another embodiment in which the separating member is in the form of a plate 2. Preferably, the plate is substantially flat or planar. However, in other embodiments, such as embodiments illustrated in FIGS. 11A, 11B, 12A and 12B, the plate 2 may be curved or angular.

In the embodiment of FIGS. 8 to 10, the tubular shaft housing 12' is fixed to the non-sampling side of the plate 2. This embodiment is advantageously simple to manufacture. As most clearly seen in FIGS. 8 and 10B, in this embodiment, there are gaps between the scoops 7 and the separating member 2. The bevelled leading edge 17 of the scoops 7 serves to direct any powder entrapped in the slits towards the outside of the scoop such that it does not disturb, or form part of, the captured sample. However, a cover can be added to further reduce powder carry over from the non-sampling side as shown in FIGS. 10D and 10E.

FIG. 14 illustrates another embodiment of a sampling device, having a plurality of scoops 7 disposed in a grid array on a separating member in the form of a plate 2. In the example illustrated, by way of example only, twelve scoops 7 are arranged in a three-by-four grid arrangement to enable collection of sampling in triplicate at four sampling depths. In other embodiments, the number of sampling depths and the number of samples collected at each depth may vary. In other embodiments a plurality of scoops may be arranged in an irregularly spaced arrangement.

The scoop volume is preferably selectable to facilitate collection of a predetermined quantity of particulate material. FIGS. 15A to 15D illustrate interchangeable scoops insertable to a separating member to enable selection of scoop volume.

In another embodiment, as shown in FIG. 16, the third vane of the separating member is movable, or rotatable, relative to the first vane thereby to enable selection of the scoop volume.

It will be appreciated that the illustrated invention can advantageously collect samples from either free-flowing or cohesive powders or granules with minimal disruption of the sample granules during insertion of the device and collection of the samples, resulting in samples that are accurately representative of the blend homogeneity at the sample location. Preferred embodiments of the device can also simultaneously collect samples from multiple sample depths, and/or collect multiple samples at each sampling depth.

Preferred embodiments of the sampling device advantageously provide a unit dose powder sampling device that greatly reduces or simply avoids the problems found with existing sampling devices. This is achieved by separating any disturbance the insertion of the probe causes to the granule bed from the area targeted for sampling, and subsequently encapsulating the sample of particulate material, without requiring flow or movement of the particulate material that may cause changes to the composition of the collected samples. In preferred embodiments, this is advantageously achieved by a separation plate which separates the granule bed into sampling and non-sampling zones. The sampling side of the separation plate is advantageously free of any protrusions during insertion. All the elements of the sampling device (e.g. scoop, etc) are position so as be on the non-sampling side of the device when the device is to be inserted into the reservoir of particulate material, thereby to provide one or more substantially flat and smooth surfaces facing towards the sampling zone.

Further advantageous features and functionality of certain preferred embodiments of the present sampling device include:
- a relatively small cross-sectional profile such that any side shifting and compression of granules is well within the enveloped sample, with relative minor or no alteration in the overall composition of the sample collected. The front edge of the probe is formed so as to redirect particles at the sampling—non-sampling border towards the non-sampling side. Such low-profile constructions assist to improve ease of insertion into a reservoir of particulate material.
- there is no protrusion or cavity on the sampling side of the separating plate, preferably only precision cut, thin (0.6-1.2 mm) "C" shaped openings or slits 8 (i.e. thin precision cuts 8) that allow the sampling scoops to turn and pass therethrough during movement between the sampling/non-sampling positions. During insertion of the sampling device, these openings/slits are filled in by the leading edge of the sampling scoops, thereby to close the openings/slits and thus preventing passage of particulate matter therethrough and reducing the space for entrapped particles. When the scoop moves to from the non-sampling position to the sampling position so as to envelop the sample, the leading edge can act to push or otherwise clear out most of the fine particles that may be trapped therein. By positioning the leading edge of each scoop within its associated opening/lit to close the openings/slits and the smooth polished sampling surface of the separation plate, the present sampling devices advantageously functions such that there is essentially no drag down of particles during insertion into the reservoir of particulate material which would contaminate the sample.

the sampling device envelops the sample of particulate material with minimal or no movement of the captured particles, thereby to avoid those problems when capturing samples of flowing material that are encountered by many existing devices. This helps to ensure that a consistent sample volume of material is taken, including when sampling both free flowing granules/powder or cohesive blends, and when sampling at any position within the reservoir (i.e. when sampling at any depth from the top to the bottom of the granule bed).

the sampling device is relatively easier to use for collection of samples in any position within a reservoir, with less training required for operators. Furthermore, the nature of the sample taken is less dependent on the skill of the operator, thereby to reduce variation in results from one operator to the next.

the ability to connect a plurality of identical sampling devices together via suitable connecting elements to enable collection of multiple samples to be taken at each sampling level during a single insertion and sampling operation provides advantages in terms of improvements in the efficiency, time and cost of the sampling process.

Although the invention has been described with reference to specific examples it will be appreciated by those skilled in the art that the invention may be embodied in many other forms.

The invention claimed is:

1. A sampling device, including:
an elongate separating member having a sampling side and a non-sampling side, the elongate separating member having a central hub and a plurality of elongate vanes extending outwardly from the central hub; wherein
a first vane of the plurality of elongate vanes extends outwardly from the central hub along a radial plane of the central hub, the first vane having a thickness; and wherein
a second vane of the plurality of vanes extends outwardly from the central hub along a respective offset plane which is parallel to a respective radial plane of the central hub, wherein the respective offset plane is offset from the respective radial plane of the central hub by a distance equal to approximately half the thickness of the first vane; wherein
each elongate vane has a height which substantially corresponds to a height of the elongate separating member; wherein
at least two adjacent vanes of the plurality of elongate vanes have a flat smooth sampling side surface extending substantially over a full height of an associated vane, thereby to define the sampling side of the elongate separating member; wherein
the elongate separating member has one or more through openings extending from the sampling side to the non-sampling side, the elongate separating member being adapted for insertion into a reservoir of particulate material, thereby to define a sampling zone and a non-sampling zone within the reservoir;
a shaft operably associated with the separating member, the shaft positioned away from the sampling side and selectively rotatable about a longitudinal axis; and
one or more sample capturing scoops attached to the shaft so that the one or more sample capturing scoops is aligned with one or more openings in a one to one correspondence with the one or more sample capturing scoops, the one or more sample capturing scoops having a leading edge, a trailing edge and a cavity for receiving a sample of particulate material; wherein
a rotation of the shaft about the longitudinal axis causes a corresponding rotation of the one or more sample capturing scoops between a first position in which the leading edge of an associated one of the one or more sample capturing scoops is located within a respective opening such that the respective opening is effectively closed and a remainder of the one or more sample capturing scoops projects away from the sampling side such that the sampling side of the separating member is free of protuberances during insertion into the reservoir, and a second position in which the one or more sample capturing scoops is positioned on the sampling side and the leading edge of an associated one of the one or more sample capturing scoops bears against the sampling side of the elongate separating member, thereby to enclose the sample of particulate material by the rotation of the scoop towards the second position.

2. The sampling device according to claim 1, wherein the one or more sample capturing scoops has an outer shell arranged about the cavity for capturing particulate material therein and wherein the outer shell is substantially axisymmetric about a rotational axis of the scoop.

3. The sampling device according to claim 1, including a plurality of scoops arranged in a spaced linear array along the length of the separating member such that each scoop captures a sample of particulate material at one of a plurality of predetermined sampling depths.

4. The sampling device according to claim 3, including connecting formations for connecting a plurality of sampling devices in parallel, thereby to enable collection of a corresponding plurality of samples at the plurality of predetermined sampling depths.

5. The sampling device according to claim 4, wherein the connecting formations are configured to enable connection of the plurality of sampling devices in a closed ring formation.

6. The sampling device according to claim 1, including a locking mechanism for selectively releasably locking the scoops in the first position or the second position or both the first and second positions.

7. The sampling device according to claim 1, wherein the leading edge of the associated scoop is substantially flush with a surface of the sampling side when the scoop is in the first position.

8. The sampling device according to claim 1, wherein the trailing edge of each scoop bears against a surface of the non-sampling side of the separating member when the scoop is in the first position.

9. The sampling device according to claim 1, wherein the trailing edge of each scoop is located within the respective opening such that the respective opening is effectively closed when the one or more sample capturing scoops is in the second position.

10. The sampling device according to claim 1, wherein each scoop has a top surface, a bottom surface and a side wall extending between the top surface and bottom surface, thereby to define the cavity for receiving particulate material.

11. The sampling device according to claim 1, wherein each opening in the separating member is configured to ensure substantially size-for-size matching with a profile of an associated one of the one or more sample capturing scoops.

12. The sampling device according to claim 1, wherein each opening is a thin precision cut on the separating member.

13. The sampling device according to claim 1, wherein each opening is C- or U-shaped.

14. The sampling device according to claim 13, wherein each C- or U-shaped opening has a width in the range of 0.5-1.5 mm.

15. The sampling device according to claim 14, wherein each C- or U-shaped opening has a width in the range of 0.6-1.2 mm.

16. The sampling device according to claim 1, wherein each opening is configured such that a portion of the elongate separating member is configured to cover the one or more sample capturing scoops when the one or more sample capturing scoops is in the first position.

17. The sampling device according to claim 1, wherein the at least two adjacent vanes of the plurality of elongate vanes are bevelled at an operationally lower end thereof so as to direct particles towards the non-sampling side during insertion into the reservoir of particulate material.

18. The sampling device according to claim 1, wherein the elongate separating member has three elongate vanes extending outwardly from the central hub.

19. The sampling device according to claim 1, wherein the elongate separating member has four elongate vanes extending outwardly from the central hub.

20. The sampling device according to claim 1, wherein the shaft is housed within the central hub.

* * * * *